(12) United States Patent
Sengun et al.

(10) Patent No.: US 10,758,337 B2
(45) Date of Patent: Sep. 1, 2020

(54) BICEPS REPAIR DEVICE

(71) Applicant: Medos International Sarl, Le Locle OT (CH)

(72) Inventors: Mehmet Z. Sengun, Canton, MA (US); Gregory R. Whittaker, Stoneham, MA (US); Benjamin Cleveland, Weymouth, MA (US); David R. Diduch, Charlottesville, VA (US); Mark H. Getelman, Tarzana, CA (US); James J. Mahoney, Hyde Park, MA (US); Jacob A. Marks, Foxboro, MA (US); Gerome Miller, Randolph, MA (US); Matthew J. Ravenscroft, Mere (GB); Howard C. Tang, Boston, MA (US)

(73) Assignee: MEDOS INTERNATIONAL SARL, Le Locle (CH)

(*) Notice: Subject to any disclaimer, the term of this patent is extended or adjusted under 35 U.S.C. 154(b) by 333 days.

(21) Appl. No.: 15/611,365

(22) Filed: Jun. 1, 2017

(65) Prior Publication Data
US 2017/0265988 A1 Sep. 21, 2017

Related U.S. Application Data

(62) Division of application No. 14/693,276, filed on Apr. 22, 2015, now Pat. No. 9,693,856.

(51) Int. Cl.
*A61F 2/08* (2006.01)
*A61B 17/04* (2006.01)

(52) U.S. Cl.
CPC ........ *A61F 2/0811* (2013.01); *A61B 17/0401* (2013.01); *A61F 2/0805* (2013.01);
(Continued)

(58) Field of Classification Search
CPC ............................ A61B 17/0401–2017/0464
See application file for complete search history.

(56) References Cited

U.S. PATENT DOCUMENTS

| 651,949 A | 6/1900 | Lillie |
| 775,427 A * | 11/1904 | Lusted .................... B25B 23/12 81/451 |

(Continued)

FOREIGN PATENT DOCUMENTS

| AU | 2013201310 B2 | 5/2015 |
| CN | 1378439 A | 11/2002 |

(Continued)

OTHER PUBLICATIONS

European Search Report for EP Application No. 17165749.7, dated Aug. 21, 2017.
(Continued)

*Primary Examiner* — Zade Coley

(57) ABSTRACT

Methods and devices are provided for anchoring a ligament or tendon to bone. In general, various inserter tools are provided for simultaneously delivering an expandable sheath and an expander into bone. With both components of the implant mounted on the same tool, the sheath and a ligament can be advanced into a bone hole and the expander, which trails behind the sheath during delivery of the sheath, can be advanced into the sheath to expand the sheath and anchor the sheath and ligament within the bone hole.

14 Claims, 18 Drawing Sheets

(52) U.S. Cl.
CPC ............... *A61B 2017/0403* (2013.01); *A61B 2017/0409* (2013.01); *A61F 2002/0835* (2013.01); *A61F 2002/0841* (2013.01); *A61F 2002/0858* (2013.01); *A61F 2002/0888* (2013.01)

(56) References Cited

U.S. PATENT DOCUMENTS

| | | |
|---|---|---|
| 1,426,320 A | 8/1922 | Reid |
| 1,925,385 A | 9/1933 | Humes et al. |
| 2,243,717 A | 5/1941 | Godoy |
| 2,288,584 A | 6/1942 | Longfellow |
| 2,381,050 A | 8/1945 | Hardinge |
| 2,484,655 A | 10/1949 | Shreve |
| 3,073,189 A | 1/1963 | Paige |
| 3,089,359 A | 5/1963 | Poulin |
| 3,103,926 A | 9/1963 | Cochran et al. |
| 3,130,763 A | 4/1964 | Bernard et al. |
| 3,298,410 A | 1/1967 | Noboru |
| 4,503,737 A | 3/1985 | DiGiovanni |
| 4,512,344 A | 4/1985 | Barber |
| 4,592,346 A | 6/1986 | Jurgutis |
| 4,640,271 A | 2/1987 | Lower |
| 4,641,640 A | 2/1987 | Griggs |
| 4,687,392 A | 8/1987 | Bidwell |
| 4,704,055 A | 11/1987 | Guhring |
| 4,711,232 A | 12/1987 | Fischer et al. |
| 4,773,417 A | 9/1988 | Moore et al. |
| 4,851,005 A | 7/1989 | Hunt et al. |
| 4,858,810 A | 8/1989 | Intlekofer et al. |
| 4,871,289 A | 10/1989 | Choiniere |
| 4,901,717 A | 2/1990 | Moore et al. |
| 4,919,130 A | 4/1990 | Stoy et al. |
| 4,921,383 A | 5/1990 | Fischer |
| 4,950,270 A | 8/1990 | Bowman et al. |
| 4,960,420 A | 10/1990 | Goble et al. |
| 4,976,715 A | 12/1990 | Bays et al. |
| 4,988,351 A | 1/1991 | Paulos et al. |
| 5,026,376 A | 6/1991 | Greenberg |
| 5,029,573 A | 7/1991 | Chow |
| 5,105,690 A | 4/1992 | Lazzara et al. |
| 5,116,337 A | 5/1992 | Johnson |
| 5,129,906 A | 7/1992 | Ross et al. |
| 5,180,384 A | 1/1993 | Mikhail |
| 5,209,756 A | 5/1993 | Seedhom et al. |
| 5,211,647 A | 5/1993 | Schmieding |
| 5,226,714 A | 7/1993 | Wright |
| 5,226,890 A | 7/1993 | Ianniruberto et al. |
| 5,234,435 A | 8/1993 | Seagrave, Jr. |
| 5,236,445 A | 8/1993 | Hayhurst et al. |
| 5,242,418 A | 9/1993 | Weinstein |
| 5,258,012 A | 11/1993 | Luscombe et al. |
| 5,266,075 A | 11/1993 | Clark et al. |
| 5,273,024 A | 12/1993 | Menon et al. |
| 5,290,296 A | 3/1994 | Phillips |
| 5,290,297 A | 3/1994 | Phillips |
| 5,314,427 A | 5/1994 | Goble et al. |
| 5,320,626 A | 6/1994 | Schmieding |
| 5,325,868 A | 7/1994 | Kimmelstiel |
| 5,325,883 A | 7/1994 | Orr |
| 5,352,229 A | 10/1994 | Goble et al. |
| 5,352,231 A | 10/1994 | Brumfield et al. |
| 5,380,334 A | 1/1995 | Torrie et al. |
| 5,383,878 A | 1/1995 | Roger et al. |
| 5,385,541 A | 1/1995 | Kirsch et al. |
| 5,409,493 A | 4/1995 | Greenberg |
| 5,425,490 A | 6/1995 | Goble et al. |
| 5,425,733 A | 6/1995 | Schmieding |
| 5,445,642 A | 8/1995 | McNulty et al. |
| 5,454,811 A | 10/1995 | Huebner |
| 5,456,721 A | 10/1995 | Legrand |
| 5,478,329 A | 12/1995 | Ternamian |
| 5,505,735 A | 4/1996 | Li |
| 5,527,341 A | 6/1996 | Gogolewski et al. |
| 5,571,104 A | 11/1996 | Li |
| 5,601,558 A | 2/1997 | Torrie et al. |
| 5,601,562 A | 2/1997 | Wolf et al. |
| 5,607,432 A | 3/1997 | Fucci |
| 5,630,805 A | 5/1997 | Ternamian |
| 5,632,748 A | 5/1997 | Beck, Jr. et al. |
| 5,651,790 A | 7/1997 | Resnick et al. |
| 5,653,763 A | 8/1997 | Errico et al. |
| 5,655,330 A | 8/1997 | Parsons, III |
| 5,658,289 A | 8/1997 | Boucher et al. |
| 5,660,186 A | 8/1997 | Bachir |
| 5,662,655 A | 9/1997 | Laboureau et al. |
| 5,662,657 A | 9/1997 | Carn |
| 5,669,925 A | 9/1997 | Saunders |
| 5,676,499 A | 10/1997 | Tukala |
| D388,171 S | 12/1997 | Fekete |
| 5,700,266 A | 12/1997 | Harryman, II |
| 5,702,398 A * | 12/1997 | Tarabishy ............ A61F 2/0811 606/104 |
| 5,713,903 A | 2/1998 | Sander et al. |
| 5,720,753 A | 2/1998 | Sander et al. |
| 5,738,666 A | 4/1998 | Watson et al. |
| 5,746,743 A | 5/1998 | Greenberg |
| 5,779,707 A | 7/1998 | Bertholet et al. |
| 5,782,865 A | 7/1998 | Grotz |
| RE36,020 E | 12/1998 | Moore et al. |
| 5,895,351 A | 4/1999 | Nottage et al. |
| 5,897,565 A | 4/1999 | Foster |
| 5,899,906 A | 5/1999 | Schenk |
| 5,899,938 A | 5/1999 | Sklar et al. |
| 5,904,685 A | 5/1999 | Walawalkar |
| 5,906,632 A | 5/1999 | Bolton |
| 5,941,882 A | 8/1999 | Jammet et al. |
| 5,948,000 A | 9/1999 | Larsen et al. |
| 5,948,001 A | 9/1999 | Larsen |
| 5,957,953 A | 9/1999 | DiPoto et al. |
| 5,961,520 A | 10/1999 | Beck, Jr. et al. |
| 5,961,521 A | 10/1999 | Roger |
| 5,968,078 A | 10/1999 | Grotz |
| 5,993,458 A | 11/1999 | Vaitekunas et al. |
| 6,024,758 A | 2/2000 | Thal |
| 6,027,523 A | 2/2000 | Schmieding |
| 6,077,267 A | 6/2000 | Huene |
| 6,117,139 A | 9/2000 | Shino |
| 6,123,711 A | 9/2000 | Winters |
| 6,143,016 A | 11/2000 | Bleam et al. |
| 6,143,017 A | 11/2000 | Thal |
| 6,221,107 B1 * | 4/2001 | Steiner .................. A61F 2/0811 623/13.13 |
| 6,231,606 B1 | 5/2001 | Graf et al. |
| 6,251,119 B1 | 6/2001 | Addis |
| 6,270,518 B1 | 8/2001 | Pedlick et al. |
| D448,482 S | 9/2001 | Bellofatto et al. |
| 6,283,948 B1 | 9/2001 | McKernan et al. |
| 6,306,138 B1 | 10/2001 | Clark et al. |
| 6,319,270 B1 | 11/2001 | Grafton et al. |
| 6,325,805 B1 | 12/2001 | Ogilvie et al. |
| 6,379,361 B1 | 4/2002 | Beck, Jr. et al. |
| 6,405,863 B1 | 6/2002 | Dhindsa |
| 6,443,956 B1 | 9/2002 | Ray |
| 6,464,706 B1 | 10/2002 | Winters |
| 6,517,519 B1 | 2/2003 | Rosen et al. |
| 6,517,564 B1 * | 2/2003 | Grafton ............... A61B 17/0401 606/213 |
| 6,533,816 B2 | 3/2003 | Sklar |
| 6,544,281 B2 * | 4/2003 | ElAttrache ......... A61B 17/0401 606/232 |
| 6,554,862 B2 | 4/2003 | Hays et al. |
| 6,558,389 B2 | 5/2003 | Clark et al. |
| 6,562,044 B1 | 5/2003 | Cooper |
| 6,579,295 B1 | 6/2003 | Supinski |
| 6,592,587 B1 | 7/2003 | Roger |
| 6,599,290 B2 | 7/2003 | Bailey et al. |
| 6,613,065 B2 | 9/2003 | Lajtai |
| 6,632,245 B2 | 10/2003 | Kim |
| 6,663,605 B2 | 12/2003 | Chan |
| 6,673,115 B2 | 1/2004 | Resch et al. |
| 6,702,817 B2 | 3/2004 | Beger et al. |
| 6,712,822 B2 | 3/2004 | Re et al. |
| 6,755,815 B2 | 6/2004 | Schultz |

(56) References Cited

U.S. PATENT DOCUMENTS

| | | |
|---|---|---|
| 6,755,836 B1 | 6/2004 | Lewis |
| 6,780,188 B2 | 8/2004 | Clark et al. |
| 6,827,722 B1 | 12/2004 | Schoenefeld |
| 6,871,740 B1 | 3/2005 | Cao |
| 6,875,214 B2 | 4/2005 | Supinski |
| 6,875,216 B2 * | 4/2005 | Wolf ............... A61B 17/863 606/304 |
| 6,887,271 B2 | 5/2005 | Justin et al. |
| 6,939,379 B2 | 9/2005 | Sklar |
| 6,942,664 B1 | 9/2005 | Voor et al. |
| 6,955,678 B2 | 10/2005 | Gabriel et al. |
| 7,074,203 B1 * | 7/2006 | Johanson ............ A61F 2/0805 411/34 |
| 7,083,647 B1 | 8/2006 | Sklar et al. |
| 7,104,999 B2 | 9/2006 | Overaker |
| 7,204,839 B2 | 4/2007 | Dreyfuss et al. |
| 7,235,060 B2 | 6/2007 | Kraus |
| 7,261,716 B2 * | 8/2007 | Strobel ............ A61B 17/8615 606/232 |
| 7,309,346 B2 | 12/2007 | Martinek |
| 7,309,355 B2 | 12/2007 | Donnelly et al. |
| 7,329,272 B2 | 2/2008 | Burkhart et al. |
| 7,341,591 B2 | 3/2008 | Grinberg |
| 7,341,592 B1 | 3/2008 | Walters et al. |
| 7,413,542 B2 | 8/2008 | Kucklick et al. |
| 7,442,202 B2 | 10/2008 | Dreyfuss |
| 7,468,074 B2 | 12/2008 | Caborn et al. |
| 7,476,228 B2 | 1/2009 | Abdou |
| 7,481,830 B2 | 1/2009 | Wall et al. |
| 7,556,638 B2 | 7/2009 | Morgan et al. |
| 7,572,283 B1 | 8/2009 | Meridew |
| 7,588,575 B2 | 9/2009 | Colleran et al. |
| 7,611,521 B2 | 11/2009 | Lubbers et al. |
| 7,651,528 B2 | 1/2010 | Montgomery et al. |
| 7,697,861 B2 | 4/2010 | Shindo et al. |
| D615,572 S | 5/2010 | Harpaz |
| 7,713,300 B2 | 5/2010 | Meridew et al. |
| 7,736,364 B2 | 6/2010 | Stone |
| 7,766,920 B2 * | 8/2010 | Ciccone ............ A61B 17/1615 606/104 |
| 7,828,090 B2 | 11/2010 | Drivdahl et al. |
| 7,833,244 B2 | 11/2010 | Cerundolo |
| 7,837,731 B2 | 11/2010 | Sklar |
| 7,883,510 B2 | 2/2011 | Kim et al. |
| 7,909,826 B2 | 3/2011 | Serhan et al. |
| 7,918,288 B2 | 4/2011 | Drivdahl et al. |
| 7,922,730 B2 | 4/2011 | Raines, Jr. |
| 7,959,650 B2 | 6/2011 | Kaiser et al. |
| 7,963,952 B2 | 6/2011 | Wright, Jr. et al. |
| 7,963,983 B2 | 6/2011 | Cerundolo |
| 7,967,861 B2 | 6/2011 | Montgomery et al. |
| 7,993,369 B2 | 8/2011 | Dreyfuss |
| 8,012,083 B2 | 9/2011 | Kucklick et al. |
| 8,021,403 B2 | 9/2011 | Wall et al. |
| 8,034,083 B2 | 10/2011 | Abdelgany et al. |
| 8,043,308 B2 | 10/2011 | Bittenson |
| 8,048,158 B2 | 11/2011 | Hays et al. |
| 8,051,929 B2 | 11/2011 | Drivdahl et al. |
| 8,057,524 B2 | 11/2011 | Meridew |
| 8,075,575 B2 | 12/2011 | Gonzalez-Hernandez |
| 8,100,916 B2 | 1/2012 | Kumar et al. |
| 8,123,749 B2 * | 2/2012 | Serhan ............ A61B 17/0642 606/75 |
| 8,128,658 B2 | 3/2012 | Kaiser et al. |
| 8,187,309 B2 | 5/2012 | Castaneda et al. |
| 8,202,295 B2 | 6/2012 | Kaplan |
| 8,206,446 B1 | 6/2012 | Montgomery |
| 8,216,131 B2 | 7/2012 | Kucklick |
| 8,221,455 B2 | 7/2012 | Shurnas et al. |
| 8,221,498 B2 | 7/2012 | Boucher et al. |
| 8,226,714 B2 | 7/2012 | Beck, Jr. et al. |
| 8,231,654 B2 | 7/2012 | Kaiser et al. |
| 8,241,298 B2 | 8/2012 | Sengun et al. |
| 8,273,086 B2 | 9/2012 | Serhan et al. |
| 8,277,464 B2 | 10/2012 | Bittenson |
| 8,282,651 B2 * | 10/2012 | Ciccone ............ A61B 17/1615 606/104 |
| 8,292,555 B2 | 10/2012 | Shaffer |
| 8,328,716 B2 | 12/2012 | Schmieding et al. |
| 8,343,195 B2 | 1/2013 | Rathbun et al. |
| 8,348,972 B2 | 1/2013 | Soltz et al. |
| 8,361,152 B2 | 1/2013 | McCormack et al. |
| 8,377,089 B2 | 2/2013 | Lipchitz et al. |
| 8,430,909 B2 | 4/2013 | Dreyfuss |
| 8,435,293 B2 | 5/2013 | Donnelly et al. |
| 8,435,294 B2 | 5/2013 | Montgomery et al. |
| 8,465,545 B2 | 6/2013 | Montgomery et al. |
| 8,506,573 B2 | 8/2013 | Dreyfuss et al. |
| 8,512,376 B2 | 8/2013 | Thornes |
| 8,512,405 B2 | 8/2013 | Baird |
| 8,523,902 B2 | 9/2013 | Heaven et al. |
| 8,523,903 B2 | 9/2013 | Kilburn-Peterson et al. |
| 8,529,610 B2 | 9/2013 | Graf et al. |
| 8,535,377 B2 | 9/2013 | Myers et al. |
| 8,545,535 B2 | 10/2013 | Hirotsuka et al. |
| 8,562,680 B2 | 10/2013 | Hays et al. |
| 8,608,765 B1 | 12/2013 | Jurbala |
| 8,617,197 B2 | 12/2013 | Friedman et al. |
| 8,617,219 B2 | 12/2013 | Oren et al. |
| 8,636,799 B2 | 1/2014 | Sklar et al. |
| 8,647,385 B2 | 2/2014 | Boucher et al. |
| 8,663,279 B2 | 3/2014 | Burkhart et al. |
| 8,663,325 B2 | 3/2014 | Graf et al. |
| 8,672,960 B2 | 3/2014 | Briganti et al. |
| 8,672,967 B2 | 3/2014 | DiMatteo et al. |
| 8,672,968 B2 | 3/2014 | Stone et al. |
| 8,721,650 B2 | 5/2014 | Fanton et al. |
| 8,747,470 B2 | 6/2014 | Beck, Jr. et al. |
| 8,758,227 B2 | 6/2014 | Kucklick et al. |
| 8,771,223 B2 | 7/2014 | Patton et al. |
| 8,771,303 B1 | 7/2014 | Jurbala |
| 8,778,023 B2 | 7/2014 | Sklar |
| 8,784,431 B1 | 7/2014 | Harder et al. |
| 8,790,368 B2 | 7/2014 | Sullivan et al. |
| 8,821,383 B2 | 9/2014 | Mirza et al. |
| 8,821,527 B2 | 9/2014 | Farnan et al. |
| 8,821,557 B2 * | 9/2014 | Corradi ............ A61B 17/064 606/308 |
| 8,840,665 B2 | 9/2014 | Young et al. |
| 8,845,725 B2 | 9/2014 | Barwood et al. |
| 8,870,877 B2 | 10/2014 | Koogle, Jr. |
| 8,932,354 B2 | 1/2015 | Barwood et al. |
| 8,939,983 B2 | 1/2015 | Stone et al. |
| 8,956,410 B2 | 2/2015 | Donnelly et al. |
| 9,056,010 B2 | 6/2015 | Shea et al. |
| 9,060,748 B2 | 6/2015 | Housman et al. |
| 9,060,772 B2 | 6/2015 | Gonzalez-Hernandez |
| 9,095,331 B2 | 8/2015 | Hernandez et al. |
| 9,241,783 B2 | 1/2016 | Trenhaile et al. |
| 9,277,911 B2 | 3/2016 | Hernandez |
| 9,289,283 B2 | 3/2016 | Baird |
| 9,301,751 B2 | 4/2016 | Sullivan et al. |
| 9,314,240 B2 * | 4/2016 | Paulk ............... A61B 17/0401 |
| 9,693,856 B2 | 7/2017 | Sengun et al. |
| 9,795,412 B2 | 10/2017 | Sinha |
| 9,833,229 B2 | 12/2017 | Hernandez et al. |
| 10,231,823 B2 | 3/2019 | Piccirillo et al. |
| 10,231,824 B2 | 3/2019 | Piccirillo et al. |
| 2001/0021855 A1 | 9/2001 | Levinson |
| 2002/0077631 A1 | 6/2002 | Lubbers et al. |
| 2002/0151977 A1 | 10/2002 | Paes et al. |
| 2002/0164218 A1 | 11/2002 | Aguirre |
| 2002/0188301 A1 | 12/2002 | Dallara et al. |
| 2003/0125749 A1 | 7/2003 | Yuan et al. |
| 2003/0153921 A1 | 8/2003 | Stewart et al. |
| 2003/0153926 A1 | 8/2003 | Schmieding et al. |
| 2003/0225456 A1 | 12/2003 | Ek |
| 2003/0233095 A1 | 12/2003 | Urbanski et al. |
| 2004/0068262 A1 | 4/2004 | Lemos et al. |
| 2004/0073219 A1 | 4/2004 | Skiba et al. |
| 2004/0073222 A1 | 4/2004 | Koseki |
| 2004/0176767 A1 | 9/2004 | Bickley |
| 2004/0193217 A1 | 9/2004 | Lubbers et al. |

(56) References Cited

U.S. PATENT DOCUMENTS

| | | |
|---|---|---|
| 2004/0230194 A1 | 11/2004 | Urbanski et al. |
| 2004/0267361 A1 | 12/2004 | Donnelly et al. |
| 2005/0075668 A1* | 4/2005 | Lizardi .............. A61B 17/0401 606/232 |
| 2005/0251137 A1 | 11/2005 | Ball |
| 2006/0004378 A1 | 1/2006 | Raines et al. |
| 2006/0015110 A1 | 1/2006 | Pepper |
| 2006/0100627 A1 | 5/2006 | Stone et al. |
| 2006/0116685 A1 | 6/2006 | Urbanski et al. |
| 2007/0005068 A1 | 1/2007 | Sklar |
| 2007/0156153 A1 | 7/2007 | Jiang et al. |
| 2007/0162124 A1 | 7/2007 | Whittaker |
| 2007/0255172 A1 | 11/2007 | Pflueger |
| 2007/0288031 A1 | 12/2007 | Dreyfuss et al. |
| 2008/0027430 A1 | 1/2008 | Montgomery et al. |
| 2008/0109038 A1 | 5/2008 | Steiner et al. |
| 2008/0161864 A1 | 7/2008 | Beck et al. |
| 2008/0215060 A1 | 9/2008 | Garcia et al. |
| 2008/0228186 A1 | 9/2008 | Gall et al. |
| 2008/0228224 A1 | 9/2008 | Sauer et al. |
| 2008/0275431 A1 | 11/2008 | Stone et al. |
| 2008/0275469 A1 | 11/2008 | Fanton et al. |
| 2009/0112270 A1 | 4/2009 | Lunn et al. |
| 2009/0138043 A1 | 5/2009 | Kohm |
| 2009/0171400 A1 | 7/2009 | van der Burg et al. |
| 2009/0192608 A1 | 7/2009 | Paulos |
| 2009/0275994 A1 | 11/2009 | Phan et al. |
| 2009/0281581 A1 | 11/2009 | Berg |
| 2009/0287259 A1 | 11/2009 | Trenhaile et al. |
| 2009/0312763 A1 | 12/2009 | McCormack et al. |
| 2009/0312782 A1 | 12/2009 | Park |
| 2009/0318923 A1 | 12/2009 | Burkhart et al. |
| 2010/0016869 A1 | 1/2010 | Paulk et al. |
| 2010/0069958 A1 | 3/2010 | Sullivan et al. |
| 2010/0106194 A1 | 4/2010 | Bonutti et al. |
| 2010/0121348 A1* | 5/2010 | van der Burg ..... A61B 17/0401 606/139 |
| 2010/0130989 A1 | 5/2010 | Bourque et al. |
| 2010/0145395 A1 | 6/2010 | Graf et al. |
| 2010/0174369 A1 | 7/2010 | Wang et al. |
| 2010/0198271 A1 | 8/2010 | Leone |
| 2010/0217393 A1 | 8/2010 | Theofilos |
| 2010/0241124 A1 | 9/2010 | Housman et al. |
| 2010/0249801 A1 | 9/2010 | Sengun et al. |
| 2011/0004247 A1 | 1/2011 | Lechmann et al. |
| 2011/0009885 A1 | 1/2011 | Graf et al. |
| 2011/0015675 A1 | 1/2011 | Howard et al. |
| 2011/0071579 A1 | 3/2011 | Reach, Jr. |
| 2011/0098727 A1 | 4/2011 | Kaiser et al. |
| 2011/0106013 A1 | 5/2011 | Whittaker et al. |
| 2011/0106252 A1 | 5/2011 | Barwood et al. |
| 2011/0106253 A1 | 5/2011 | Barwood et al. |
| 2011/0112550 A1 | 5/2011 | Heaven et al. |
| 2011/0112558 A1 | 5/2011 | Whayne et al. |
| 2011/0251621 A1 | 10/2011 | Sluss et al. |
| 2011/0257691 A1 | 10/2011 | Sutterlin et al. |
| 2011/0270323 A1 | 11/2011 | Olsen et al. |
| 2012/0010668 A1 | 1/2012 | Shimko |
| 2012/0057949 A1 | 3/2012 | Canizares, Jr. et al. |
| 2012/0059379 A1 | 3/2012 | Homan et al. |
| 2012/0109156 A1 | 5/2012 | Overes et al. |
| 2012/0109299 A1 | 5/2012 | Li et al. |
| 2012/0116459 A1 | 5/2012 | Nottmeier |
| 2012/0130374 A1 | 5/2012 | Bouduban et al. |
| 2012/0136357 A1 | 5/2012 | Torrie et al. |
| 2012/0150190 A1 | 6/2012 | Rabiner et al. |
| 2012/0150301 A1 | 6/2012 | Gamache et al. |
| 2012/0211543 A1 | 8/2012 | Euteneuer |
| 2012/0215232 A1 | 8/2012 | Olsen et al. |
| 2012/0245686 A1 | 9/2012 | Park |
| 2012/0316565 A1 | 12/2012 | Stark |
| 2013/0006302 A1* | 1/2013 | Paulk ................. A61B 17/0401 606/232 |
| 2013/0103054 A1* | 4/2013 | Housman ........... A61B 17/0401 606/139 |
| 2013/0103080 A1 | 4/2013 | Hernandez |
| 2013/0125714 A1 | 5/2013 | Dahners |
| 2013/0158597 A1 | 6/2013 | Hernandez |
| 2013/0158664 A1 | 6/2013 | Palmatier et al. |
| 2013/0190817 A1 | 7/2013 | Bouduban et al. |
| 2013/0197534 A1 | 8/2013 | Lauderbaugh et al. |
| 2013/0197591 A1 | 8/2013 | Corradi et al. |
| 2013/0238036 A1 | 9/2013 | Sinha |
| 2013/0267998 A1* | 10/2013 | Vijay ................. A61B 17/0401 606/232 |
| 2013/0268010 A1 | 10/2013 | Santangelo et al. |
| 2013/0310842 A1 | 11/2013 | Winkler et al. |
| 2013/0325128 A1 | 12/2013 | Perloff et al. |
| 2013/0331942 A1 | 12/2013 | Baird |
| 2013/0338710 A1 | 12/2013 | Heaven et al. |
| 2014/0005686 A1 | 1/2014 | Patton et al. |
| 2014/0046369 A1 | 2/2014 | Heaven et al. |
| 2014/0081324 A1 | 3/2014 | Sengun |
| 2014/0107713 A1 | 4/2014 | Pech et al. |
| 2014/0171983 A1 | 6/2014 | Graf et al. |
| 2014/0172095 A1 | 6/2014 | Graf et al. |
| 2014/0188166 A1 | 7/2014 | Cobb et al. |
| 2014/0228898 A1 | 8/2014 | Gordon |
| 2014/0236183 A1 | 8/2014 | Graf et al. |
| 2014/0243978 A1 | 8/2014 | Beck, Jr. et al. |
| 2014/0243982 A1 | 8/2014 | Miller |
| 2014/0249579 A1 | 9/2014 | Heaven et al. |
| 2014/0257384 A1 | 9/2014 | Dreyfuss et al. |
| 2014/0277133 A1 | 9/2014 | Foerster |
| 2014/0277134 A1* | 9/2014 | ElAttrache ......... A61B 17/0401 606/232 |
| 2014/0309668 A1 | 10/2014 | Sullivan et al. |
| 2014/0343604 A1 | 11/2014 | Frank |
| 2014/0364862 A1 | 12/2014 | Bennett et al. |
| 2015/0018878 A1 | 1/2015 | Rizk et al. |
| 2015/0018947 A1 | 1/2015 | Barwood |
| 2015/0039030 A1 | 2/2015 | Saliman et al. |
| 2015/0066042 A1 | 3/2015 | Cummins et al. |
| 2015/0173741 A1 | 6/2015 | Housman et al. |
| 2015/0190130 A1* | 7/2015 | Groh ................. A61B 17/0401 606/232 |
| 2015/0238327 A1 | 8/2015 | Cheng et al. |
| 2016/0113643 A1 | 4/2016 | Diduch et al. |
| 2016/0113644 A1 | 4/2016 | Diduch et al. |
| 2016/0113756 A1 | 4/2016 | Diduch et al. |
| 2016/0113757 A1* | 4/2016 | Diduch .............. A61B 17/8872 606/104 |
| 2016/0113758 A1 | 4/2016 | Diduch et al. |
| 2016/0310260 A1 | 10/2016 | Sengun et al. |
| 2017/0290655 A1 | 10/2017 | Piccirillo et al. |
| 2017/0290656 A1 | 10/2017 | Piccirillo et al. |
| 2018/0296319 A1 | 10/2018 | Diduch et al. |
| 2018/0344376 A1 | 12/2018 | Diduch et al. |
| 2019/0029805 A1 | 1/2019 | Piccirillo et al. |
| 2019/0029806 A1 | 1/2019 | Piccirillo et al. |
| 2020/0008928 A1 | 1/2020 | Diduch et al. |
| 2020/0129171 A1 | 4/2020 | Diduch et al. |

FOREIGN PATENT DOCUMENTS

| | | |
|---|---|---|
| CN | 101394795 A | 3/2009 |
| CN | 102098969 A | 6/2011 |
| CN | 102292032 A | 12/2011 |
| CN | 102438548 A | 5/2012 |
| CN | 102470007 A | 5/2012 |
| CN | 202515702 U | 11/2012 |
| CN | 102905629 A | 1/2013 |
| CN | 103209647 A | 7/2013 |
| CN | 103445850 A | 12/2013 |
| CN | 203789970 U | 8/2014 |
| CN | 102098968 B | 7/2015 |
| DE | 10325139 A1 | 12/2004 |
| EP | 1110510 A1 | 6/2001 |
| EP | 1491162 A2 | 12/2004 |
| EP | 2327374 A1 | 6/2011 |
| EP | 3020371 | 5/2016 |
| EP | 2918238 B1 | 11/2017 |
| JP | 200513740 A | 1/2005 |

(56) References Cited

FOREIGN PATENT DOCUMENTS

| | | |
|---|---|---|
| JP | 2005-66135 A | 3/2005 |
| JP | 2005-506864 A | 3/2005 |
| JP | 2005-323700 A | 11/2005 |
| JP | 2007-50269 A | 3/2007 |
| JP | 2007-306979 A | 11/2007 |
| JP | 200886769 A | 4/2008 |
| JP | 2011516795 A | 5/2011 |
| JP | 2011-528270 A | 11/2011 |
| JP | 2014-171673 A | 9/2014 |
| WO | 9428799 A1 | 12/1994 |
| WO | 199731517 A3 | 8/1997 |
| WO | WO-0130253 A1 | 5/2001 |
| WO | WO-2007110863 A2 | 10/2007 |
| WO | 2009055800 A1 | 4/2009 |
| WO | 2012125905 A1 | 9/2012 |
| WO | 2012129206 A2 | 9/2012 |
| WO | WO-2012129617 A1 | 10/2012 |
| WO | WO-2012138777 A1 | 10/2012 |
| WO | 2014150053 A1 | 9/2014 |

OTHER PUBLICATIONS

Translation of Chinese Search Report for CN Application 201510696510.1 dated May 26, 2019 (4 pages).

Search Report for CN Application No. 201510696528.1 dated Jun. 25, 2019 (16 pages).

Chinese Search Report issued in related CN Application No. 201510696822.2 (5 pages).

Translation of International Search Report for CN Application No. 201510697570.5 dated Mar. 1, 2019 (3 pages).

European Search Report for EP Application No. 15191001.5, dated Apr. 1, 2016. (7 pages).

European Search Report for EP Application No. 15191002.3, dated Apr. 15, 2016. (8 pages).

European Search Report for EP Application No. 15191010.6, dated Apr. 4, 2016. (6 pages).

European Search Report for EP Application No. 15191011.4, dated Apr. 1, 2016. (6 pages).

European Search Report for EP Application No. 15191013.0, dated Apr. 14, 2016. (7 pages).

European Search Report for EP Application No. 16166686.2, dated Sep. 20, 2016. (8 pages).

European Search Report for EP Application No. 17165700.0, dated Aug. 11, 2017. (12 pages).

U.S. Appl. No. 14/693,276, filed Apr. 22, 2015, Biceps Repair Device.

\* cited by examiner

BICEPS REPAIR DEVICE

CROSS-REFERENCE TO RELATED APPLICATIONS

The present application is a divisional of U.S. application Ser. No. 14/693,276 entitled "Biceps Repair Device," filed on Apr. 22, 2015, and incorporated by reference herein in its entirety.

FIELD

Surgical devices and methods are provided for anchoring tissue to bone, and more particularly surgical implants, delivery tools, and methods are provided for securing a biceps tendon to the humerus.

BACKGROUND

Disorders of the long head of the biceps tendon are a common source of shoulder pain and may occur in association with other diagnoses such as rotator cuff tears, superior labrum anterior posterior tears, impingement syndrome and capsular injuries, or may be present as an isolated source of shoulder pain. The treatment options for disorders of the long head of the biceps (LHB) continue to evolve and can include LHB tenodesis. In a tenodesis procedure, a suture is passed through the base of the LHB to locate the LHB in the subacromial space and to provide proximal control during the dissection. Once the suture is placed, the LHB is cut near the glenoid attachment. A sizer can be used to measure the tendon size and to thereby determine the appropriately sized bone screw. Once the screw is selected, a bone hole is drilled and a tendon fork is then used to push the tendon down into the bone hole. A bone screw is then delivered into the bone hole to anchor the tendon within the bone hole.

While current procedures can provide an effective means for anchoring a tendon to bone, they can suffer from several drawbacks. For example, current procedures require the use of numerous tools, which can lead to a prolonged procedure and increased costs. The use of a screw can also increase the risk of damage to the tendon, as rotation of the screw into the bone hole can tear or sever through the tendon. Moreover, it can be difficult to maintain the desired tension on the tendon while the screw is being implanted, as the tendon can become misaligned and or can slip during insertion of the screw. Any tension applied to the tendon during insertion of the anchor can also cause the anchor to back-out of the bone hole.

Accordingly, there remains a need for improved methods and devices for anchoring tissue to bone, and in particular for performing a biceps tenodesis.

SUMMARY

Various implants, tools and methods are provided for attaching a tendon to bone. In one embodiment, a bone anchor inserter tool is provided having an outer shaft and an inner shaft. The outer shaft can have having proximal and distal ends and an inner lumen extending at least partially therethrough, the distal end having first and second prongs extending distally therefrom. The inner shaft can extend through the inner lumen of the outer shaft and can be non-slidably fixed to the outer shaft, the inner shaft having a distal-most end terminating at a location distal to the distal end of the outer shaft and proximal to a distal-most end of the first and second prongs.

The inner shaft can have a variety of configurations, and in one embodiment the inner shaft is freely rotatable relative to the outer shaft. A distal portion of the inner shaft can be in the form of a drive tip that is configured to extend into a lumen in an implant and to apply a rotational force to the implant. In another embodiment, the inner shaft is non-rotatably fixed to the outer shaft.

The outer shaft can have a variety of configurations, and in one embodiment the distal end of the outer shaft includes viewing windows formed in opposed sidewalls thereof. The first and second prongs extending distally from the distal end of the outer shaft can also have a variety of configurations and in some aspects the first and second prongs can be elongate wires, each elongate wire having a proximal end that is fixedly disposed within a bore formed in the distal end of the outer shaft. In some aspects, the first and second prongs comprise elongate members formed from a super elastic or shape memory material.

The bone anchor inserter tool can also include various other components, such as a driver shaft having an inner lumen extending therethrough, the driver shaft being configured to be slidably and rotatably disposed between the outer shaft and the inner shaft. In some aspects, the driver shaft can include a drive tip at a distal end thereof that is configured to extend into a lumen in an implant and to apply a rotational force to the implant.

In another embodiment, a bone anchor and delivery system is provided that includes an anchor assembly and a delivery tool. The anchor assembly can include an expandable sheath having opposed slots formed therein and an inner lumen extending at least partially therethrough and an expander configured to be received within the inner lumen of the sheath to cause the sheath to expand outward, the expander having an inner lumen extending therethrough. The delivery tool can include an outer shaft having first and second prongs extending distally from a distal end thereof and configured to extend along opposed slots formed in the sheath, and an inner shaft extending through and mated to the outer shaft such that the inner shaft is prevented from sliding axially relative to the outer shaft. In the bone anchor and delivery system, the prongs of the outer shaft can be positioned to extend along the opposed slots in the sheath and the expander can be disposed within the outer shaft proximal of the sheath, the inner shaft can extend through the inner lumen in the expander and a distal end of the inner shaft can abut against a distal inner surface of the sheath such that the inner shaft can apply a force to the sheath to advance the sheath into a bone hole.

The inner shaft can have a variety of configurations, and in one embodiment the inner shaft is freely rotatable relative to the outer shaft. The inner shaft can include a drive tip that is configured to extend into a drive recess formed in the expander for driving the expander into the sheath. In another embodiment, the inner shaft can be non-rotatably fixed to the outer shaft.

The bone anchor and delivery system can also include various other components, such as a driver shaft having an inner lumen extending therethrough, the driver shaft being slidably and rotatably disposed within the outer shaft, and the inner shaft being disposed through the inner lumen of the driver shaft. The driver shaft can include a drive tip at a distal end thereof that is configured to extend into a drive recess in the expander for driving the expander into the sheath.

In yet another embodiment, a method of implanting an anchor in bone is provided that includes positioning a sheath coupled to a distal end of an outer shaft of an inserter tool adjacent to a ligament to be advanced into a bone hole, and manipulating the inserter tool to advance the sheath and the ligament into the bone hole, the inserter tool having an inner shaft extending through the outer shaft, the inner shaft applying a force to a distal end of the sheath to advance the sheath and the ligament into the bone hole. The method also includes manipulating the inserter tool to advance an expander disposed over the inner shaft into the sheath, the expander causing the sheath to expand outward and engage the bone hole to thereby anchor the ligament within the bone hole.

The method can include manipulating the inserter tool to advance the expander into the sheath comprises rotating the inner shaft relative to the outer shaft to cause the expander to be threaded into the sheath. The inner shaft can be prevented from translating relative to the outer shaft. In some embodiments, the expander is at least partially threaded into the sheath when the sheath is advanced into the bone hole. In some embodiments, manipulating the inserter tool to advance the expander into the sheath includes axially translating a driver shaft through the outer shaft and over the inner shaft.

In yet further embodiment, a method for anchoring tissue to bone is provided that can include manipulating an inserter tool to advance a sheath coupled to a distal end of the inserter tool and to advance a tendon positioned around the sheath into a bone hole. The inserter tool can have a handle with a drive shaft extending distally from the handle, and an expander positioned proximal of the sheath and disposed on a distal end of the drive shaft such that the expander trails the sheath as the sheath and the tendon are advanced into the bone hole. The method can further include rotating the handle of the inserter tool to rotate the drive shaft and thereby cause the expander to rotate, wherein threads on the expander engage corresponding threads formed within the sheath to advance the expander distally into the sheath. The expander can cause the sheath to expand outward to thereby anchor the sheath and the tendon within the bone hole.

BRIEF DESCRIPTION OF THE DRAWINGS

The embodiments described above will be more fully understood from the following detailed description taken in conjunction with the accompanying drawings. The drawings are not intended to be drawn to scale. For purposes of clarity, not every component may be labeled in every drawing. In the drawings.

DETAILED DESCRIPTION

Figure 1A:
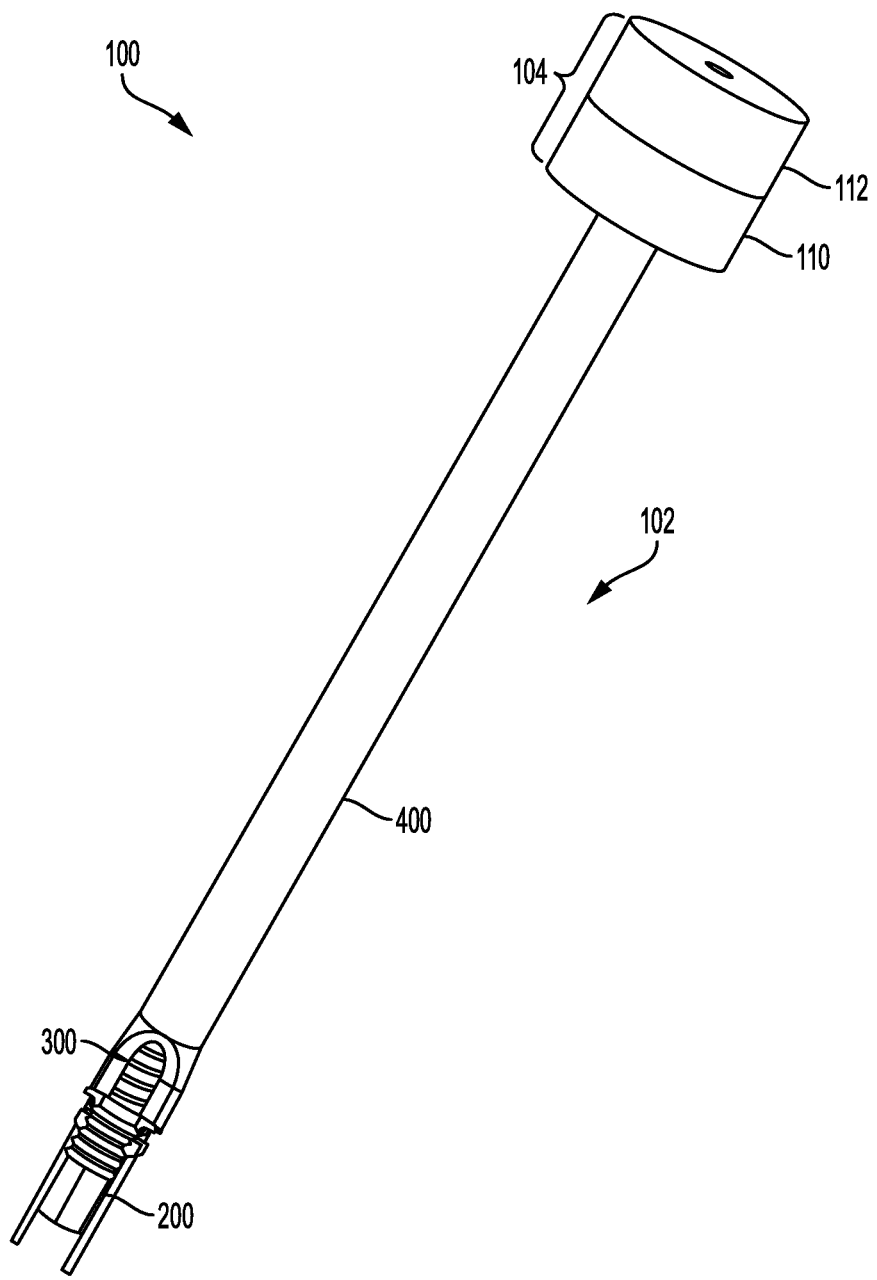
FIG. 1A is a perspective view of one embodiment of a biceps tenodesis system having a sheath, an expander, and an inserter tool including an outer shaft and an inner shaft.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

In general, methods and devices are provided for anchoring a ligament or tendon to bone. In an exemplary embodiment, the methods and devices are used to perform a biceps tenodesis surgery, however, a person skilled in the art will appreciate that the devices and methods can be used in various procedures and for anchoring any tissue to bone. In exemplary embodiments, various inserter tools are provided for delivering a bone anchor having both an expandable sheath and an expander into a bone hole to anchor a tendon or other issue within the bone hole. The described system is configured as a so-called "all-in-one" device that can be used to both insert the sheath into a bone hole and advance the expander into the sheath to expand the sheath outward and thereby anchor a tendon in the bone hole. Thus, separate tools for inserting the sheath and then driving the expander thereto are not required. Accordingly, the system has a reduced number of components, which can reduce the number of steps (and therefore, amount of time) required to perform a biceps tenodesis procedure. The entire attachment preparation procedure can be straightforward and requires a surgeon to take only a few quick steps to affix the implant structure including the sheath and the expander to the bone. Also, the surgery can be performed with minimal risk of injuring to the tendon. The sheath can be anchored without rotating the sheath, which can eliminate or reduce a possibility of undesirable twisting of the tendon. In addition, the described techniques can help save operating room costs.

Figure 1B:
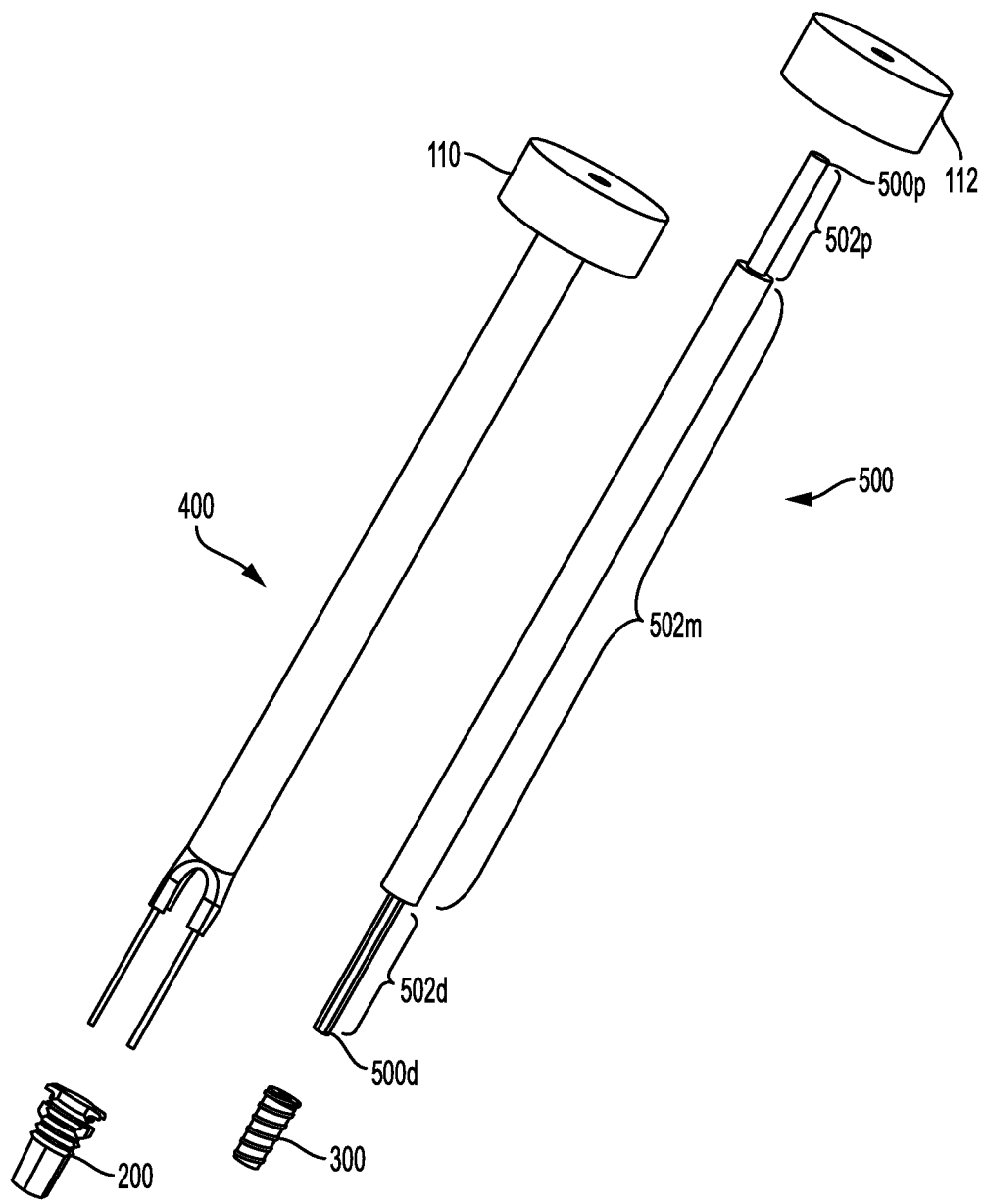
FIG. 1B is an exploded side perspective view of the biceps tenodesis system of FIG. 1A.

FIGS. 1A and 1B illustrate one embodiment of a biceps tenodesis system 100 including an inserter or delivery tool 102 that includes an outer shaft 400, an inner shaft 500, and a handle assembly 104 coupled to proximal ends of the outer and inner shafts 400, 500. By way of example only, the tool is shown coupled to an expandable sheath 200 and an expander 300. As shown in FIG. 1A, in the assembled configuration, the expandable sheath 200, expander 300, and outer and inner shafts 400, 500 are disposed so that their longitudinal axis can coincide. The inserter tool 102 is configured to be coupled to both the expander 300 and the sheath 200, and to apply a force to a distal end of the sheath 200 and thus advance the sheath 200 with a tendon disposed therearound into a bone hole. The expander 300 is configured to be received within a lumen extending at least partially through the expandable sheath 200 to thereby expand the sheath 200. The inserter tool 102 also causes the expander 300 to advance into the lumen of the sheath 200 to expand the sheath 200. In this way, the system 100 is used as an "all-in-one" device configured to both deliver the tendon or ligament into the bone hole and lock the sheath 200 within the bone hole.

Figure 2C:
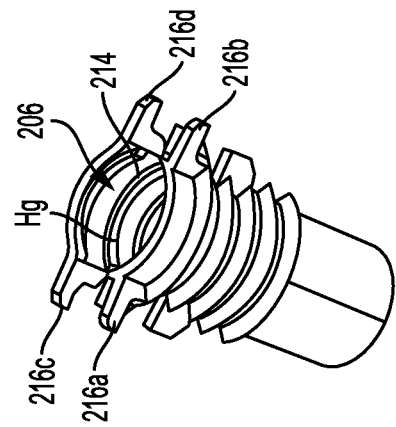
FIG. 2C is another perspective view of the sheath of FIG. 1A.
Figure 2A:
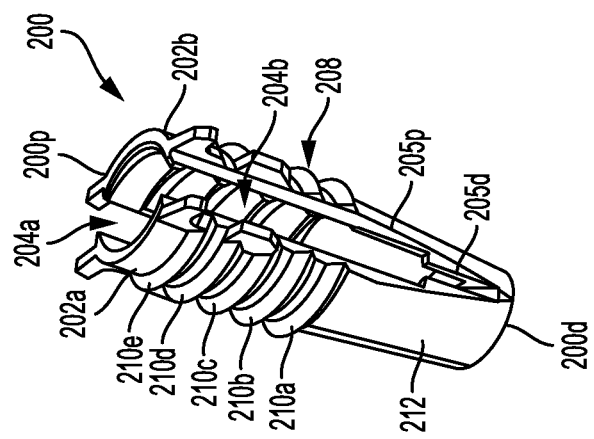
FIG. 2A is a side perspective view of the sheath of FIG. 1A.
Figure 2B:
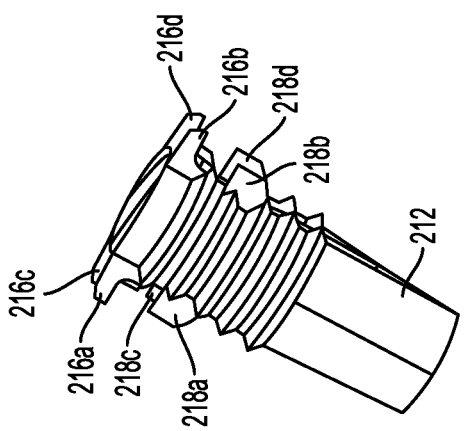
FIG. 2B is another side perspective view of the sheath of FIG. 1A.

FIGS. 2A-2C illustrate the expandable sheath 200 of FIGS. 1A and 1B in more detail. In general, the sheath is configured to seat a tendon therearound, and to receive the expander 300 therein which is effective to cause the sheath to expand into bone to anchor the tendon within a bone hole. The sheath can be formed from any bio-compatible material, and, in some embodiments, it can be bio-absorbable. The shape and configuration of the sheath can vary. By way of example, the sheath 200 can be configured as described at least in U.S. patent application Ser. No. 14/610,602, entitled "Biceps Tenodesis Implants and Delivery Tools," filed Jan. 30, 2015, the contents of which are incorporated herein by reference in their entirety.

In general, the sheath 200 has a generally elongate cylindrical shape, with a circular or oval cross-sectional geometry. The sheath 200 is configured to move from a collapsed position to an expanded position and has a proximal end 200p and a distal end 200d, as shown in FIG. 2A. The sheath 200 can be a split sheath, with first and second sidewalls 202a, 202b that are connected at the distal end 200d and that are separated by first and second elongated slots 204a, 204b extending therebetween. The elongate slots 204a, 204b can have any suitable configuration. For example, in some embodiments, as shown in FIG. 2A, the slots can have a distal portion 205d having a width that is less than a width at a proximal portion 205p. As shown, the sheath 200 has an inner lumen 206 defined by the inner surfaces of the first and second sidewalls 202a, 202b and extending at least partially through the sheath 200.

The distal end 200d of the sheath 200 can be solid and closed. In the illustrated embodiment, both the sheath 200 and the expander 300 are configured to be axially aligned and disposed on the same tool, and a guidewire to guide the expander into the sheath 200 may not be needed. However, in some embodiments, the guidewire can be used. In such embodiments, an inner surface (not shown) of the distal end 200d of the sheath 200 can include a bore formed therein that is configured to receive a guidewire therethrough. Also, although some of the figures show a guidewire bore in the distal end of the sheath 200, it should be appreciated that the guidewire bore may not be necessary if the guidewire is not used.

As shown in FIG. 2C, the sheath 200 can also include a distal facing surface that is concave or saddled to seat the tendon thereon, and a convex proximal surface on each sidewall 202a, 202b. The sheath 200 can also include various surface features formed thereon or therein to facilitate engagement with the bone and the expander 300. In one embodiment, a proximal portion 208 of the sheath 200 can have ribs 210a, 210b, 210c, 210d, 210e that allow the sheath to be inserted into bone without the need to rotate the sheath, while a distal portion 212 of the sheath can be free of surface features. As shown in FIGS. 2A and 2C, the sheath 200 includes threads 214 formed on the internal surface of the sidewalls 202a, 202b for threadably mating with the expander 300. In some embodiments, the sheath 200 can include anti-plunge tabs 216a, 216b, 216c, 216d formed at the proximal end 200p to prevent over-insertion of the sheath 200 into the bone hole, and/or cortical retaining tabs 218a, 218b, 218c, 218d positioned along the mid-section of the sheath 200 and configured to be positioned just beneath the cortical bone and within cancellous bone when the sheath 200 is implanted in a bone hole. The sheath 200 can additionally or alternatively include any other suitable features. For example, the sheath 200 can include anti-collapse tabs discussed in more detail in U.S. patent application Ser. No. 14/610,602. One skilled in the art will appreciate that the sheath 200 can include any other suitable features.

Figure 3A:
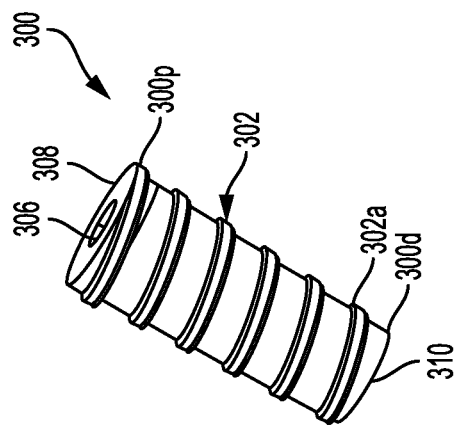
FIG. 3A is a side perspective view of the expander of FIG. 1A.

As indicated above, the sheath 200 is configured to receive the expander 300 and is effective to expand the sheath 200 to anchor the sheath 200 and tendon coupled thereto within a bone hole. As shown in FIG. 3A, in one embodiment, the expander 300 is in the form of a screw having a generally cylindrical shape that tapers distally inward to a reduced diameter along at least a distal portion of the length thereof. The expander 300 has a thread 302 formed on the outer surface thereof and extending along the entire length of the expander 300 to facilitate engagement with the sheath 200. In some embodiments, as shown in FIGS. 1A and 2A-2C, at least a distal portion 302a of the thread 302 can be engaged, or "pre-threaded," into the proximal end 200p of the sheath 200 when the expander 300 and the sheath 200 are mounted on the inserter tool, as will be discussed below.

The expander 300 can be fully cannulated so that it has a bore or inner lumen 306 defined therein. The inner lumen 306 can have a shape and size corresponding to a shape and size of a drive feature configured to be received within the inner lumen 306 so as to rotate the expander 300. In the illustrated embodiment, the inner lumen 306 is in the form of a hexagonal drive socket configured to receive a hexagonal distal portion 502d of the inner shaft 500 to thereby allow the inner shaft 500 to rotate the expander 300. The distal portion 502d of the inner shaft 500 can be inserted into the inner lumen 306 as to extend along a portion of the entire length of the lumen 306. A person skilled in the art will appreciate, however, that other configurations of the inner lumen 306 can be used.

As further shown in FIG. 3A, the expander 300 can have a flat proximal facing surface 308 and a flat distal facing surface 310. The proximal surface 308 and the distal surface 310, however, can have various shapes and the shape can be configured to conform to the sheath and/or the bone surface. A length of the expander 300 can be less than, equal to, or greater than the length of the sheath 200.

A person skilled in the art will appreciate that the expander can have a variety of other configurations, and the expander can be configured to be non-rotatably inserted into the sheath, rotatably inserted into the sheath, or partially non-rotatably and partially rotatably inserted into the sheath. For example, the expander can include a proximal portion having threads formed thereon and a distal portion that is non-threaded and free of surface features. In use, the non-threaded distal portion of the expander can be non-rotatably advanced into the sheath. Once the distal portion is fully disposed within the sheath, the expander can then be rotated to thread the proximal portion into the sheath. The sheath can include corresponding threads along an entire inner surface thereof, or along on a proximal portion of the inner surface thereof, for mating with the threads on the expander.

In some embodiments, the expander can be configured to be non-rotatably inserted into the sheath. FIG. 3B illustrates an embodiment of an expander 320 that is configured to be non-rotatably advanced into a sheath. In this embodiment, the expander 320 is in the form of a plug that is pushed into the sheath. As shown in FIG. 3B, the expander 320 has a generally cylindrical shape with a constant minor diameter $D_1$ along a proximal portion 322p and a distally tapered distal portion 322d. A mid-portion 322m of the expander 320 is at least partially distally tapered. The illustrated expander 320 has a flat proximal facing surface 328. A distal facing surface 330 of the expander 320 can also be flat or it can be convex. In some embodiments, the expander 320 can be generally shaped as a bullet. The proximal portion 322p, mid-portion 322m, and the distal portion 322d can be free of any surface features and can be relatively smooth. The expander 320 can be fully cannulated such that it has a bore or inner lumen 326 extending therethrough. At least the proximal portion of the inner lumen can include a drive feature for allowing it to receive an inserter tool (e.g., an inner shaft of inserter tool 102) therein.

Figure 3C:
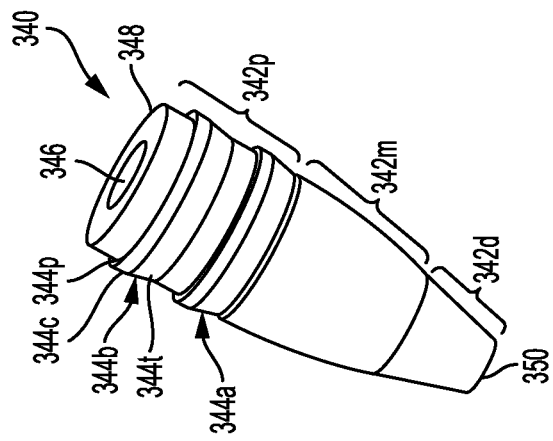
FIG. 3C is a side perspective view of yet another embodiment of an expander.
Figure 3B:
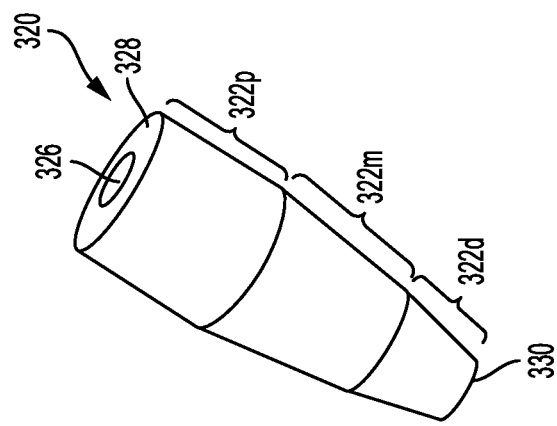
FIG. 3B is a side perspective view of another embodiment of an expander.

FIG. 3C illustrates another embodiment of an expander 340 that can be configured to be non-rotatably inserted into the sheath. As shown in FIG. 3C, the expander 340 has a generally cylindrical shape with a constant minor diameter $D_1$ along a proximal portion 342p and at least partially distally tapered mid- and distal portions 342m, 342d. A shown, the mid-portion 342m can be generally convex, although it should be appreciated that one or more portions of the mid-portion 342m may be not convex. The distal portion 342d of the expander 340 is tapered distally inward to a reduced diameter at the distal-most end of the expander 340. The illustrated mid-portion 342m and the distal portion 342d are free of any surface features and are relatively smooth. The proximal portion 342p, on the other hand, includes one or more ribs or flanges formed thereon and extending circumferentially therearound. While the proximal portion 342p is shown having two ribs 344a, 344b formed thereon and spaced longitudinally apart, the expander 340 can include any number of ribs, or other protrusions. Each rib, as shown for the rib 344b, includes a flat proximal-facing surface 344p, and an outer sidewall having a proximal constant diameter portion 344c and a distal tapering portion 344t. The ribs 344a, 344b have an outer diameter that is greater than the minor outer diameter of the expander 340. The expander 340 can have a flat proximal facing surface 348 and a flat or convex distal facing surface 350. The expander 340 can be fully cannulated for allowing it to receive an inserter tool (e.g., an inner shaft of inserter tool 102) in an inner lumen or bore 346 extending therethrough. In use, the expander 320 can be non-rotatably advanced into the sheath. The ribs 344s, 344b on the proximal portion 342p can cause the sheath to expand outward thereby anchoring the sheath within the bone hole.

As indicated above, various inserter tools are provided for delivering a sheath and expander into bone for anchoring a tendon to the bone. Referring back to FIGS. 1A and 1B, in the illustrated embodiment, the inserter tool 102 includes an outer shaft 400 and an inner shaft 500 extending through the outer shaft 400. As further shown in FIGS. 4A and 4B, the outer shaft 400 has a proximal end 400p, a distal end 400d, and a lumen 403 extending therethrough between the proximal and distal ends 400p, 400d. The proximal end 400p of the outer shaft 400 is coupled to a distal handle 110 of the handle assembly 104, as discussed in more detail below. The distal end 400d of the outer shaft 400 has a fork 401 including first and second opposed distal prongs 404, 406 extending distally therefrom. The prongs 404, 406 are configured to be positioned along the sidewall slots in the sheath 200 to prevent rotation of the sheath 200 when the inner shaft 500 is rotated to drive the expander 300 into the sheath 200.

Figure 6A:
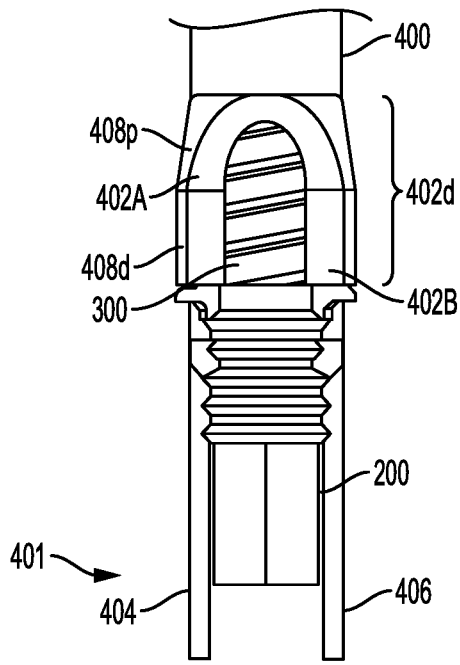
FIG. 6A is a side view of a distal portion of the system of FIG. 1A.
Figure 6B:
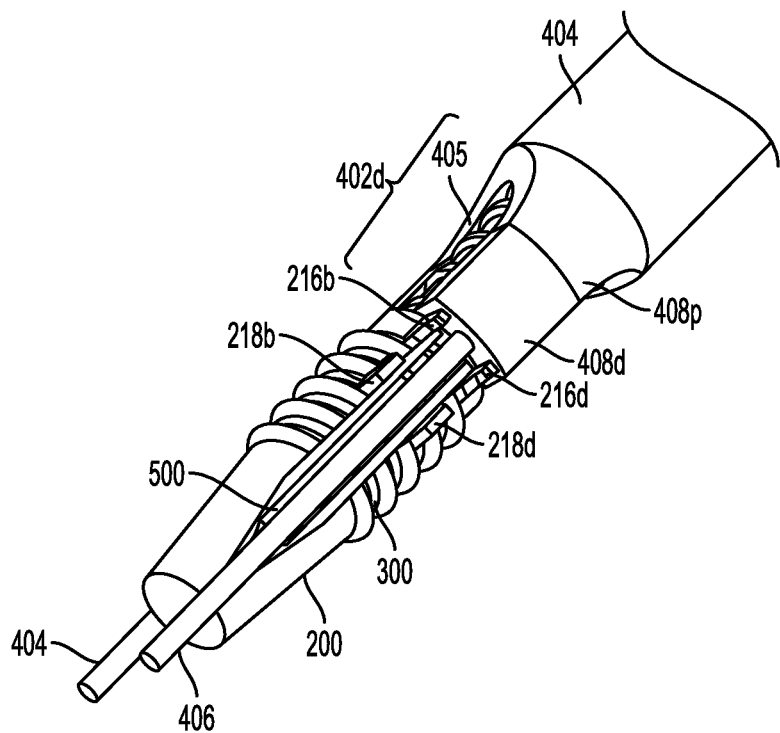
FIG. 6B is a side perspective view of a distal portion of the system of FIG. 1A.
Figure 6D:
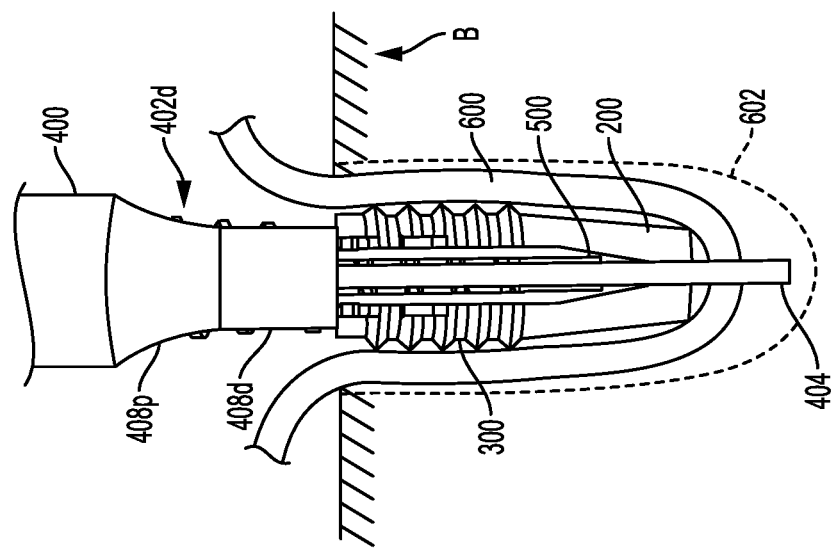
FIG. 6D is a side view of a distal portion of the system of FIG. 1A, shown in use inserting a tendon into a bone hole in bone.
Figure 6C:
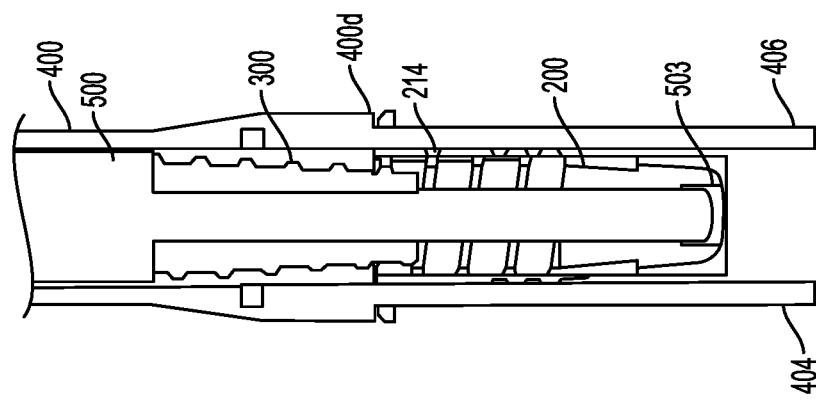
FIG. 6C is a cross-sectional view of a distal portion of the system of FIG. 1A.

The distal portion 402d of the outer shaft 400 is shown in more detail in FIGS. 6A-6D and generally has opposed arms 402A 402B with U-shaped cut-outs or window 410 formed therebetween. Each arm has a prong 404, 406, extending distally therefrom. The distal portion 402d can have an increased diameter as compared to the remainder of the shaft 400. Also, a diameter of the outer wall of the distal portion 402d of can vary along a longitudinal length thereof. For example, as shown in FIGS. 6A and 6C showing a front view of the distal portion 402d of the outer shaft 400, the distal portion 402d can have a proximal portion 408p having an outer diameter that increases distally and a distal portion 408d that can have substantially constant outer diameter.

Figure 4A:
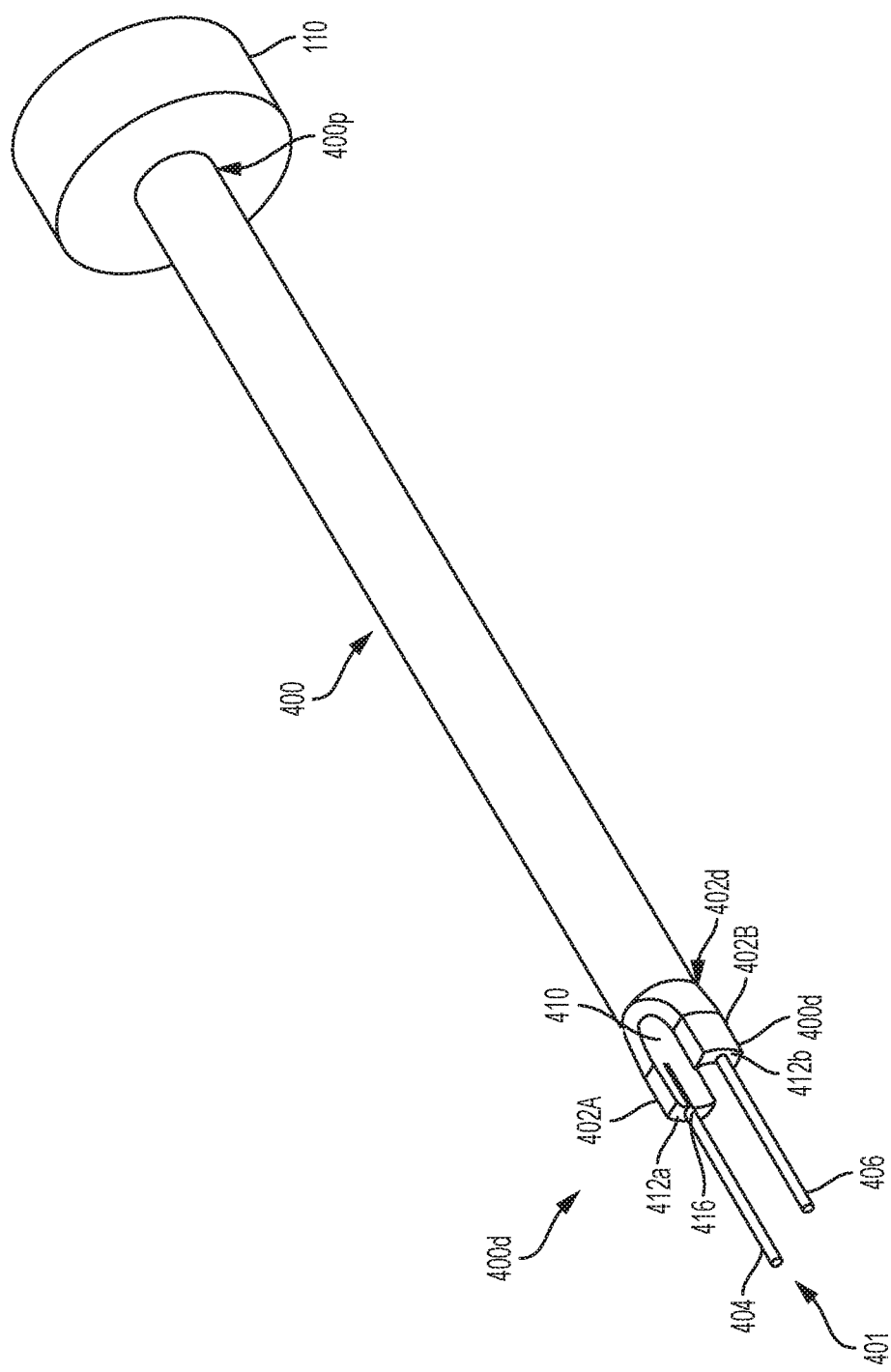
FIG. 4A is a side perspective view of the outer shaft of the inserter tool of FIG. 1A.
Figure 4B:
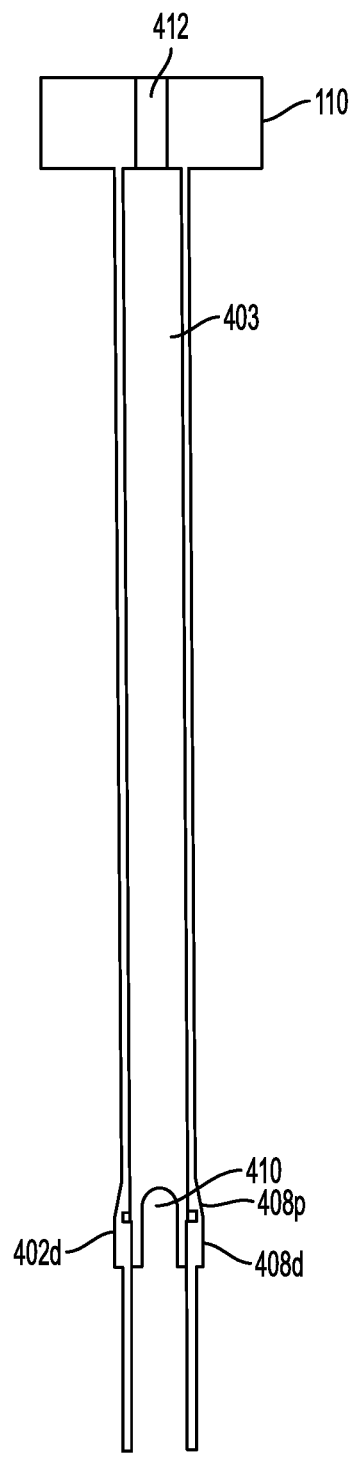
FIG. 4B is a cross-sectional view of the outer shaft of FIG. 4A.

As indicated above, the distal portion 402d can be generally arcuate or U-shaped so that it has first and second arms 402A, 402B of the "U," each coupled to one of the prongs 404, 406. The first and second arms 402A, 402B can be substantially parallel to one another and can extend distally so as to form elongated, generally upside-down U-shaped viewing windows 410 therebetween. It should be appreciated, however, that the viewing windows 410 can have any suitable shape, and the first and second arms 402A, 402B can have any suitable configuration. Additionally or alternatively, in some embodiments, at least a portion of the outer shaft 400 can be formed from a transparent material to allow viewing therethrough. As shown in FIGS. 4A and 4B, the viewing windows 410 form a common space between the first and second arms 402A, 402B. Thus, when the inner shaft 500 is inserted into the outer shaft 400 and the system 100 is assembled as shown in FIG. 1A and further in FIGS. 6A-6D, the viewing windows 410 allow at least a portion of the expander 300 coupled to the sheath 200 to be viewed therethrough.

The first and second opposed prongs 404, 406 of the distal fork 401 can have any suitable configuration and they can be coupled to the outer shaft 400 in any suitable manner. For example, in the embodiment of FIG. 4A, the first and second prongs 404, 406 are in the form of elongate wires. However, one skilled in the art will appreciate that each of the first and second prongs 404, 406 can be in the form of a rod, or any other elongate member. In the illustrated embodiment, as shown in FIG. 4A, the first and second prongs 404, 406 have a generally circular cross-section, however one skilled in the art will appreciate that the first and second prongs 404, 406 can have a generally triangular configuration or any other suitable configuration.

As shown in FIG. 4A, each of the wires has its proximal end fixedly disposed within a respective bore or slot formed in the distal portion 402d of the outer shaft 400. Thus, in FIG. 4A, a proximal end of the first prong 404 is shown by way of example as fixedly disposed within a bore 416 formed in the first arm 402A of the distal portion 402d. The bore 416 can extend through a portion of the inner wall of the arm or through the entire length of the arm. The second prong 406 is coupled to the distal end 400d in a similar manner. The proximal ends of the first and second prongs 404, 406 can be secured within the bores formed in the distal end 400d by welding, adhesives, etc. However, it should be appreciated that the prongs can be coupled to the outer shaft 400 in any suitable manner. Furthermore, in some embodiments, the first and second prongs 404, 406 can be formed integrally and/or monolithically with the outer shaft 400.

The first and second prongs can be formed from any suitable material. In some embodiments, the first and second prongs 404, 406 can be elongate members formed from a shape memory or super elastic material, such as Nitinol®, nickel-titanium based alloy, or any other shape memory or super elastic material. Thus, the prong can retain their shape even after deforming forces are applied thereto.

Referring back to FIG. 1A, when the system 100 is assembled, the sheath 200 is positioned at the distal end 400d of the outer shaft 400 such that the first and second prongs 404, 406 of the distal fork 401 extend along the elongate slots 204a, 204b in the sheath 200 and extend beyond the distal end 200d of the sheath 200. In this way, rotation of the sheath 200 during insertion of the expander into the sheath 200 is prevented. In use, as also shown in FIG. 4A, distal facing surfaces 412a, 412b of the first and second arms 402A, 402B of the distal end 400d of the outer shaft 400 abut against a proximal facing surface of the sheath 200.

Figure 5A:
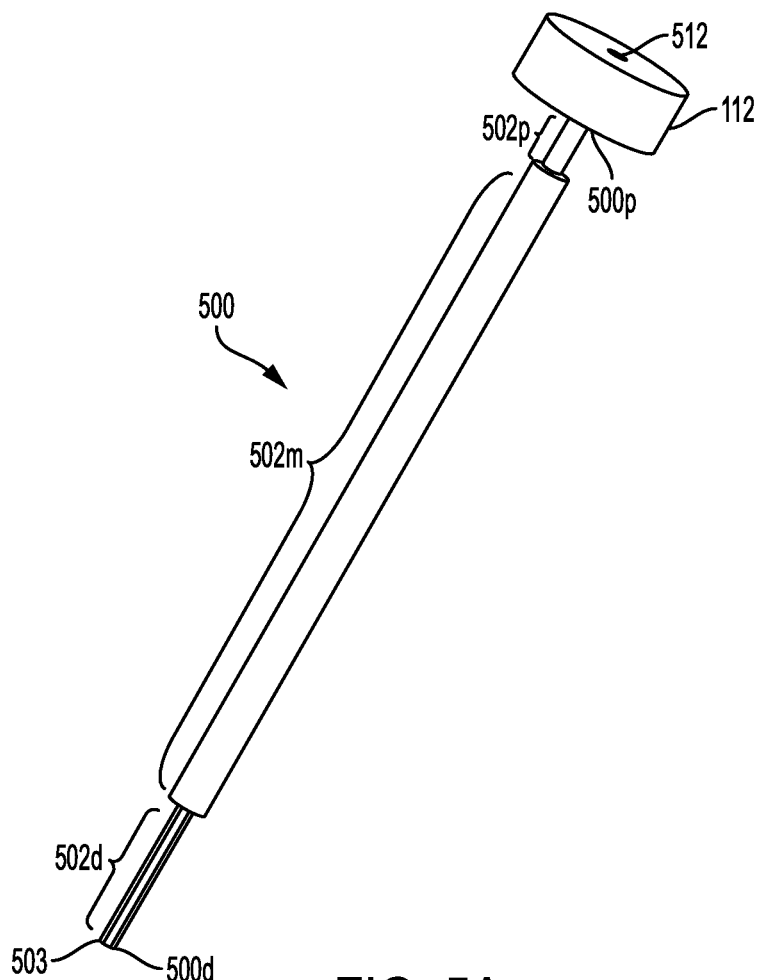
FIG. 5A is a side perspective view of the inner shaft of the inserter tool of FIG. 1A.

As indicated above, the outer shaft 400 is configured to receive the inner shaft 500 therein. As shown in FIGS. 1B and 5A, the inner shaft 500 can have a generally elongate cylindrical configuration. In an exemplary embodiment, as shown in FIGS. 1B and 5A, the inner shaft 500 is in the form of a screw driver disposed configured to be within the inner lumen of the outer shaft 400 and having a drive tip configured to extend into the expander. In one exemplary embodiment, the inner shaft 500 has a proximal end 500p configured to mate to a proximal handle 112 of the handle assembly 104, as discussed in more detail below, and a distal end 500d configured to mate to an expander. As shown in FIGS. 1B and 5A, the inner shaft 500 includes a proximal portion 502p, a distal portion 502d, and a middle portion 502m extending between the proximal and distal portions 502p, 502d. In the illustrated embodiment, an outer diameter of the middle portion 502m is greater than outer diameters of the proximal and distal portions 502p, 502d. The inner shaft 500 can rotate relative to the outer shaft 400 such that its drive tip engaging the inner lumen of the expander causes the expander to rotate and to thereby advance into the sheath, causing the sheath to expand outward within a bone hole.

Figure 5B:
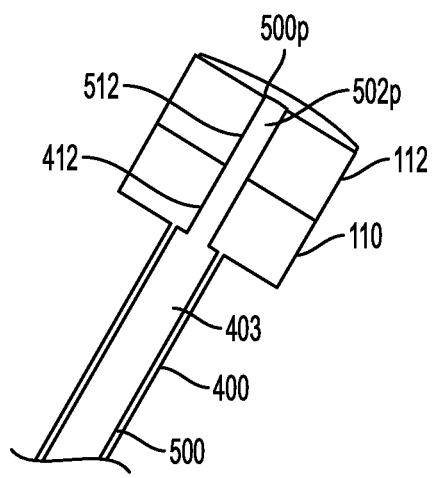
FIG. 5B is a cross-sectional view of a proximal portion of the inner shaft of FIG. 5A.

As shown in FIG. 5B, the proximal portion 502p of the inner shaft 500 has a length sufficient for the proximal portion 502p to extend through at least a portion of the handle assembly 104. As also shown in FIG. 5B, the proximal portion 502p slidably extends through a distal handle 110 coupled to the outer shaft 400 and disposed distally of the proximal handle 112 coupled to the proximal portion 502p. In this way, the inner shaft 500 maintains the proximal handle 112 at a fixed axial position relative to the distal handle 110 such that the proximal handle 112 is prevented from distal axial translation relative to the outer shaft 400.

The middle portion 502m of the inner shaft 500 extends through the outer shaft 400 such that a distal end of the middle portion 502m abuts the expander 300, as shown in FIG. 5B, and a proximal end of the middle portion 502m abuts the distal handle 110 coupled to the outer shaft 400.

In an exemplary embodiment, as shown in FIGS. 5A and 6C, the distal portion 502p of the inner shaft 500 can be in the form of a drive tip for engaging a socket in the expander. In the illustrated embodiment, the drive tip or distal portion 502d of the inner shaft 500 has a hexagonal configuration for extending into a corresponding hexagonal drive socket formed in the expander 300 to thereby allow the inner shaft 500 to rotate the expander 300. However, one skilled in the art will appreciate that the drive tip 502d can have any other configuration so as to fit within the inner lumen of the expander 300 and rotatably engage the expander 300. As shown in FIG. 6C, the distal portion 502p can extend through the expander 300 and further distally through the sheath 200. In an exemplary embodiment, a length of the distal portion 502d of the inner shaft 500 is sufficient such that the distal end 503 of the inner shaft 500 abuts the distal inner surface of the sheath 200 to apply axial force to the sheath 200 to advance the sheath 200 into a bone hole. Further, although in the illustrated embodiment a guidewire is not shown, in some embodiments the inner shaft 500 can further include a guidewire channel extending therethrough for allowing the sheath, the expander, and the inner and outer shafts to be slidably advanced over a guidewire.

When assembled, the inner shaft 500 extends through the outer shaft 400 and the drive tip extends distantly beyond the distal end of the outer shaft 400, terminating proximal to the prongs. In the illustrated embodiment, the inner shaft 500 is rotatably coupled to the outer shaft 400 so that the inner shaft 500 can rotate, but not slide distally, within the outer shaft 400. The proximal ends of the outer and inner shafts 400, 500 can be coupled to a handle assembly that allows the inner shaft 500 to rotate relative to the outer shaft 400, while preventing distal translation.

The handle assembly 104 configured to operate the inserter tool 102 can have a variety of shapes and configurations. FIGS. 1A, 1B, 4A, 4B, 5A, and 5B illustrate one exemplary embodiment of a handle assembly 104 of the inserter tool 102 coupled to the proximal ends of the outer and inner shafts 400, 500. The handle assembly 104 can be used to apply force to a distal end of the sheath to insert the sheath into a bone hole and to rotate the inner shaft to drive the expander into the sheath.

In the illustrated embodiment, the handle assembly 104 includes a distal handle 110 and a proximal handle 112 that is disposed proximally of the distal handle 110, as shown in FIG. 5B. The distal handle 110 is fixedly coupled to or integrally formed on a proximal end of the outer shaft 400 and the proximal handle 112 is coupled to or integrally formed on a proximal end of the inner shaft 500. As shown in FIG. 1B, in one embodiment, the inner shaft 500 can be removably mated to the proximal handle 112 so as to allow disassembly of the device, e.g., for cleaning. The distal handle 110 and the proximal handle 112 are shown having the shape of a disk. In the illustrated embodiment, the distal and proximal handles 110, 112 have planar distal- and proximal-facing surfaces and have substantially the same diameter. However, a person skilled in art will appreciate that the distal and proximal handles 110, 112 can have any other configuration and size to facilitate grasping. In addition, the handles 110, 112 can have various other features, such as actuators, buttons, knobs, triggers, gripping components, etc., configured to operate the inserter tool 102.

The proximal handle 112 can be operated to rotate the inner shaft 500 within a lumen of the outer shaft 400 while the distal handle 110 can be held stationary. The distal handle 110, disposed distally of the proximal handle 112, will also prevent distal axial translation of the inner shaft 500 with respect to the outer shaft 400. A person skilled in the art will appreciate that the handle assembly 104 can include any other components that facilitate interaction between the outer shaft 400 and inner shaft 500 and that are used to conveniently operate the inserter tool 102 to anchor the sheath and tendon within a bone hole.

In the illustrated embodiment, the distal handle 110 of the handle assembly 104 can be fully cannulated such that it has an inner lumen 412 extending therethrough that is coaxial with the inner lumen 403 of the outer shaft 400, as shown in FIGS. 4B and 5B. The inner lumen 412 can be configured to receive therein the proximal portion 500p of the inner shaft 500. As shown in FIGS. 5A and 5B, the proximal handle 112 has an inner lumen 512 extending at least partially therethrough and coaxial with the lumen 412 defined within the distal handle 110. As shown in FIG. 5B, the inner lumens 412, 512 extending through the handle assembly 104 can have the same or substantially the same diameter. The proximal portion 500p of the inner shaft 500 extends proximally through the inner lumen 412 of the distal handle 110 and extends proximally through the inner lumen 512 of the proximal handle 112, as also shown in FIG. 5B. While the more distal portion of the inner shaft's proximal portion 500p can rotate within the distal handle 110, the inner shaft's more proximal portion is fixedly coupled to the proximal handle 112 so that rotation of the proximal handle 112 causes the inner shaft 500 to rotate. Threads or other mating features can be used to mate the proximal portion to the proximal handle.

A person skilled in the art will appreciate that the handle assembly 104 can have other suitable configurations that allow rotating the inner shaft 500 while preventing distal sliding of the inner shaft 500 within the outer shaft 400, as the embodiments described herein are not limited to a specific mechanism. Furthermore, the handle assembly 104 can include features for controlling movement of the inner and outer shafts relative to one another. In addition, in embodiments in which a guidewire is used, the handle assembly can also include a feature for engaging the guidewire.

As indicated above, in use, prior to advancing the expander 300 into the sheath 200, the distal end of the expander 300 is partially threaded into the proximal end of the sheath 200 and the inner shaft 500 extends through both the sheath 200 and expander 300. The sheath 200 can be held on the inserter tool by friction fit between the inner lumen 206 of the sheath 200 and the drive tip 502d of the inner shaft 500 extending through the lumen 206. Thus, the sheath 200 is pressed onto the drive tip of the inner shaft 500. A surgeon can thus hold the distal handle 110 coupled to the outer shaft 400 so that the distal handle 110 remains stationary while rotating the proximal handle 112 coupled to the inner shaft 500 to thereby rotate the inner shaft 500 within the outer shaft 400. Because the proximal handle 112 abuts a proximal surface of the distal handle 110, the distal handle 110 prevents distal axial translation of the inner shaft 500 within the outer shaft 400. In this way, the inner shaft 500 rotates the expander 300 coupled thereto so as to rotatably insert the expander 300 into the sheath 200.

The system 100 described herein can be used to implant a sheath or anchor in a bone in various different ways. One exemplary method for implanting an anchor in bone, for example, to perform a biceps tenodesis surgery, is shown in connection with FIG. 6D and also with reference to FIGS. 6A-6C. While the method is described in connection with the expander 300 and sheath 200, a person skilled in the art will appreciate that the method can be performed using various anchors and tools, and that it can be performed for anchoring any tissue to any bone.

In a biceps tenodesis procedure, a biceps tendon is retrieved in a suitable manner and a size of the tendon is determined to allow a surgeon to select an appropriately sized implant and tools. Exemplary embodiments of methods and devices for determining a size of the tendon and tools to insert and retain the tendon in a bone hole are further described in U.S. application Ser. No. 14/610,602 entitled "Biceps Tenodesis Implants and Delivery Tools" filed on Jan. 30, 2015, which is hereby incorporated by reference in its entirety. Further, in some embodiments, the inserter tool 102 can be used to size the tendon by using a distal fork (e.g., fork 401). Tools having different sizes can have differently sized forks. After properly sizing the tendon, the proper size reamer can be used to ream a bore in the bone, e.g., the humorous. However, a person skilled in the art will appreciate that the bone hole can be formed using any suitable bone hole preparation techniques and devices.

The bone hole diameter can be sized to allow the fork 401 having the tendon 600 positioned between the prongs 404, 406 thereof and the sheath 200 to be easily inserted therein. The anti-plunge tabs 216a-216b prevent over insertion of the sheath into the bone hole. Alternatively, the outer shaft 400 of the inserter tool 102 may have a greater diameter compared to the tunnel 602, so that the outer shaft 400 will be prevented from entering into the bone hole 602. This is shown, for example, in FIG. 6D.

After a bone hole 602 in bone B is prepared, the sheath 200 coupled to a distal end of the inserter tool 102 can be positioned adjacent to the tendon 600 to be advanced into the bone hole 602. The system 100 including the inserter tool 102, the expander 300, and the sheath 200, can be an "all-in-one" device that can be used to first "dunk" the tendon 600 into the bone hole 602 and to then drive the expander 300 into the sheath 200 to anchor the sheath 200 in the bone hole. Thus, there may be no need for separate inserter and driver tools as the "all-in-one" device has both of these functionalities. It should be appreciated that, although not shown in connection with the described embodiments, in some embodiments, a guidewire can be additionally used.

As shown in FIGS. 6A-6D, the inserter tool 102 can have the sheath 200 and expander 300 coupled distally thereto such that the expander 300 and the sheath 200 are disposed over the inner shaft 500. The sheath 200 can held on the inner shaft 500 by friction-fit or press-fit. Alternatively or additionally the sheath can be held onto the expander 300 by "pre-threading" the expander 300 into a proximal end of the sheath 200, as shown in FIGS. 6C-6D. The expander 300 in turn is held onto the inserter tool 102. The prongs 404, 406 of the distal fork 401 on the outer shaft 400 extend along the slots in the sheath 200, as shown in FIGS. 6A-6D.

Before it is advanced into the bone hole 602, the inserter tool 102 can be manipulated to position the tendon 600 between the prongs 404, 406 of the fork 401. Once the inserter tool 102 with the sheath 200 and expander mounted thereon is properly positioned with the tendon 600 extending around the sheath 200, the inserter tool 102 can be manipulated to advance, or dunk, the tendon 600 and sheath 200 into the bone hole 602. The sheath 200 is in an unexpanded configuration during insertion and is supported by the prongs 404, 406. As discussed above, the inner shaft 500 can extend through the outer shaft 400 such that the distal-most end 503 of the inner shaft 500 abuts against a distal inner surface of the sheath 200. Thus, in the illustrated embodiment, the inner shaft 500 of the inserter tool 102 can be used to apply force to the distal end of the sheath 200 to advance the sheath 200 and the tendon 600 into the bone hole 602. The distal end of the arms on the outer shaft can also apply a distal force to the sheath, however, the majority of the force should be applied to the distal end of the sheath so as to avoid the risk of causing damage to the sheath.

After the inserter tool 102 with the sheath 200 and expander coupled thereto and the tendon 600 are advanced into the bone hole 602, the inserter tool 102 can be manipulated to drive the expander 300 into the sheath 200 to expand the sheath 200 into an expanded configuration to thus anchor it within the bone hole 602. The inner shaft 500 of the inserter tool 102 can be rotated relative to the outer shaft 400 to cause the expander to thread into the sheath. The pre-threaded configuration will cause the threads to advance the expander distally within the sheath and along the drive tip. For example, referring back to FIGS. 1A and 1B, a surgeon can hold the distal handle 110 coupled to the outer shaft 400 so that the distal handle 110 remains stationary while the proximal handle 112 coupled to the inner shaft 500 is rotated. Axial translation of the inner shaft 500 relative to the outer shaft 400 is prevented. At the same time, the outer shaft 400 remains stationary and, because the prongs 404, 406 distally coupled thereto extend into the slots in the sheath 200, the sheath 200 can be anchored while being prevented from rotating. In this way, the expander 300 will translate distally into the sheath 200 until the full length or substantially the full length of the expander 300 is driven into the sheath 200 to thereby expand the sheath 200 and anchor it within the bone hole 602. Because the sheath 200 is prevented from rotating while the expander 300 is advanced thereto, the possibility of twisting the tendon can be eliminated or reduced, which can reduce a risk of damaging the tendon.

When the distal end of the inserter tool 102 is fully inserted into the bone hole 602, the anti-plunge tabs and the distal end of the outer shaft will rest against the bone, and the cortical retaining tabs will extend below the cortical bone. The viewing windows 410 opposite one another can facilitate viewing of the expander, and they can receive the tendon 600 so as to allow outer shaft to rest against sheath. When the expander 300 is fully inserted into the sheath 200, the expander 300 will cause the sheath 200 to expand radially outward to engage the tendon 600 between the sheath 200 and the bone hole 602, and to thereby anchor the sheath and tendon within the bone hole. The ribs on the outer surface of the sheath can also engage bone to prevent back-out and tendon slippage. Once the sheath 200 is properly anchored into the bone hole to thereby anchor the tendon, the inserter tool 102 can be removed while the sheath 200 remains in the bone hole (not shown).

FIGS. 7A-8D illustrate another exemplary embodiment of a biceps tenodesis system 700 having an inserter or delivery tool 702 that includes an outer shaft 1000, an inner shaft 1100, a driver shaft 1200 disposed between the outer shaft 1000 and the inner shaft 1100, and a proximal handle assembly 704 coupled to proximal ends of the outer, inner, and driver shafts 1000, 1100, 1200. The outer shaft 1000 and the inner shaft 1100 are configured to advance a sheath 800 into a bone hole, and the driver shaft 1200 is configured to drive an expander 900 into the sheath 800. A person skilled in the art will appreciate that the implant is shown by way of example only and that the tool can be used with any implant.

In the illustrated embodiment, the inner shaft 1100 can be rigidly fixed to or integrally formed with the outer shaft 1000 and a distal end of the inner shaft 1100 can abut against a distal inner surface of the sheath 800 such that the inner shaft 1100 can apply a force to the distal end of the sheath 800 to advance the sheath 800 into a bone hole. A distal end of the driver shaft 1200 is configured to extend into a drive recess in the expander 900 and to rotate and axially translate with respect to the outer shaft 1000 to drive the expander 900 into the sheath 800.

Figure 7A:
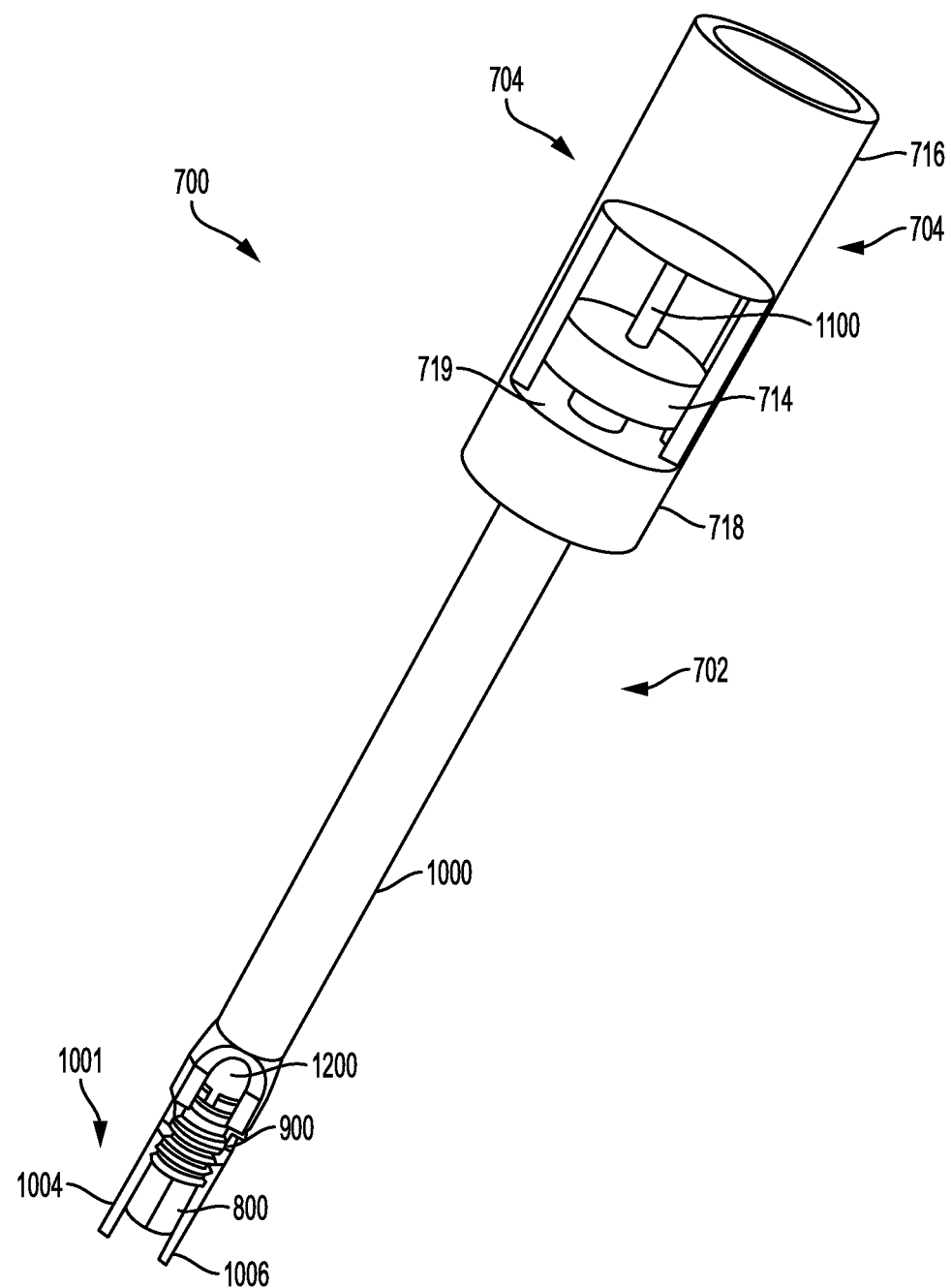
FIG. 7A is a perspective view of another embodiment of a biceps tenodesis system having a sheath, an expander, and an inserter tool including an outer shaft, an inner shaft, and a driver shaft disposed between the outer and inner shafts.
Figure 7B:
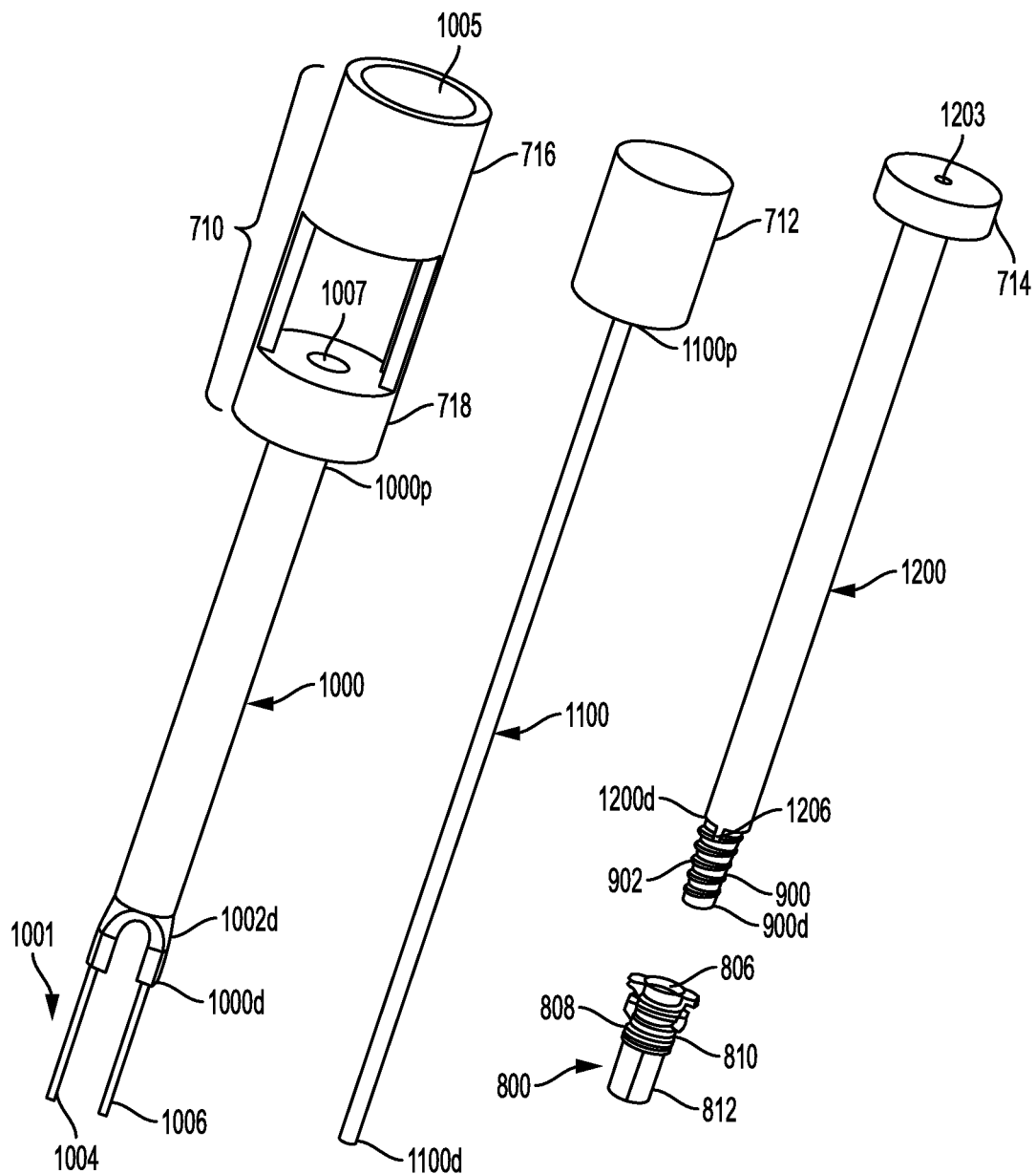
FIG. 7B is an exploded side perspective view of the biceps tenodesis system of FIG. 7A.
Figure 8B:
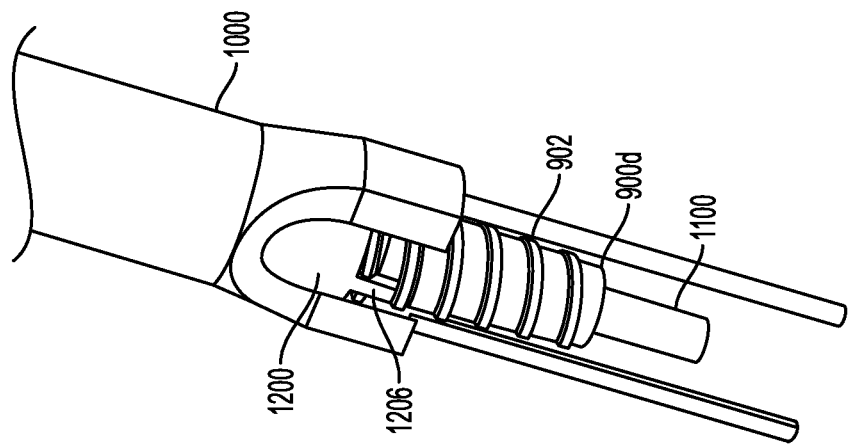
FIG. 8B is a side perspective view of a distal portion of the inserter tool of the system of FIG. 7A coupled to the expander.
Figure 8A:
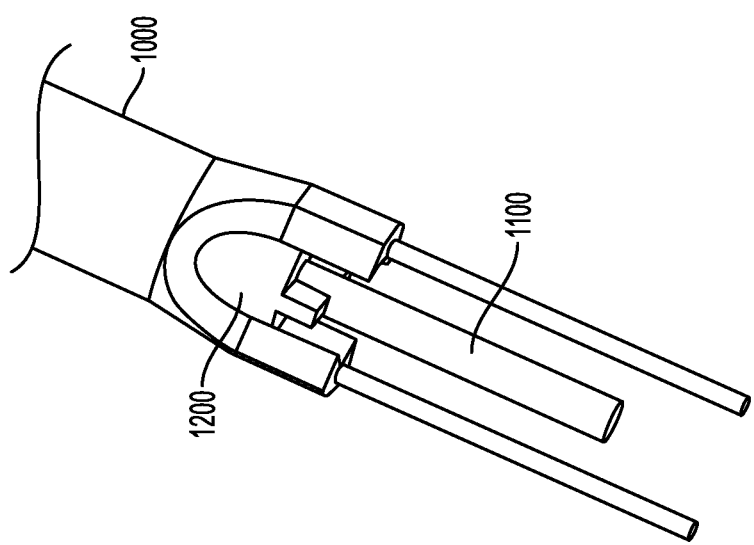
FIG. 8A is a side perspective view of a distal portion of the inserter tool of the system of FIG. 7A.
Figure 8D:
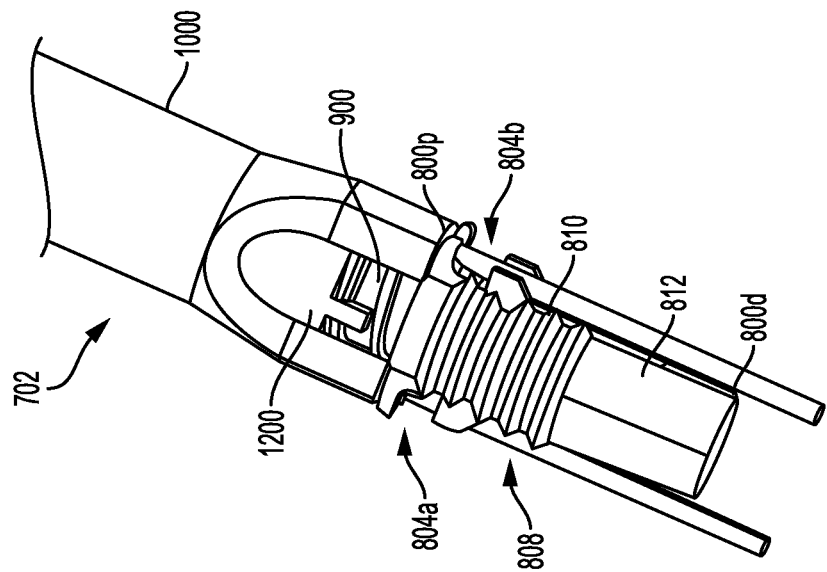
FIG. 8D is a side perspective view of a distal portion of the inserter tool of the system of FIG. 7A coupled to the expander and the sheath.

The sheath 800 can have a variety of different configurations. In the illustrated exemplary embodiment, the sheath 800 can be configured similar to sheath 200 (FIGS. 1A, 1B, 2A, 2B, and 2C). For example, like sheath 200, sheath 800 has a generally elongate cylindrical shape, with a circular or oval cross-sectional geometry. The sheath 800 has a proximal end 800*p* and a distal end 800*d* and it can be a split sheath, with first and second sidewalls that are connected at the distal end 800*d* and that are separated by first and second elongated slots 804*a*, 804*b* extending therebetween, as shown in FIG. 8D. The sheath 800 has an inner lumen 806 defined by the inner surfaces of the first and second sidewalls and extending at least partially through the sheath 800. A proximal portion 808 of the sheath 800 can have surface features, such as ribs 810 (FIGS. 7B and 8D), or any other bone-engaging surface features (e.g., threads, teeth, or other protrusions). A distal portion 812 of the sheath 800 can be free of surface features. However, in some embodiments, the distal portion 812 can include one or more surface features.

In the illustrated embodiment, the sheath 800 includes internal threads formed in its lumen 806 on inner facing surfaces of the sheath 800 for threadably mating with the expander 900. Alternatively, the inner facing surfaces may be free of threads. The sheath 800 can include other features similar to those described for sheath 200, or any other suitable features.

The expander 900 is effective to expand the sheath 800 to anchor the sheath 800 and a tendon coupled thereto within a bone hole. The expander 900 can also have a variety of different configurations. In the illustrated embodiment, the expander 900 can be configured similar to expander 300 (FIGS. 1A, 1B, 3A, 6A, 6B and 6C). Thus, as shown in FIGS. 7B and 8B, the expander 900 is in the form of a screw having a generally cylindrical shape with threads 902 formed on the outer surface thereof and extending along the entire length of the expander 900 to facilitate engagement with the sheath 800. The threads 902 can engage the internal threads formed on inner facing surfaces of the sheath 800 when the expander 900 is advanced into the sheath 800 to expand it outward. Although the expander 900 is shown as having threads formed thereon, it should be appreciated that, in some embodiments, the expander 900 can be free of threads and it can be configured, for example, similar to expander 320 in FIG. 3B or expander 340 in FIG. 3C. Other configurations of the expander 900 can be used as well. The expander screw 900 can taper distally inward to a reduced diameter along at least a portion of the length thereof. In the illustrated embodiment, the expander 900 tapers distally to a reduced diameter at a distal end 900*d* thereof.

The expander 900 can be fully cannulated so that it has an inner lumen extending therethrough. The inner lumen can be configured and sized to fit a drive tip of the driver shaft 1200. For example, the inner lumen of the expander 900 can have a hexagonal cross-section so that it can receive a hexagonal drive tip of the driver shaft 1200. The drive tip of the driver shaft 1200 can extend partially or fully through the inner lumen of the expander 900. However, one skilled in the art will appreciate that the inner lumen of the expander screw 900 can have any other suitable configuration, as embodiments are not limited in this respect. For example, in embodiments in which the expander is a push-type expander that is pushed into the sheath rather than rotatably translated thereinto, a drive feature to rotatably advance expander 900 may not be required and the inner lumen of the expander screw 900 can be cylindrical.

As shown in FIGS. 7A, 7B, and 8B-8D, the expander screw 900 can removably mate to a distal end of the driver shaft 1200, e.g., by snap-fit, press-fit, or using other suitable technique(s). In this way, the expander screw 900 can translate and, in some embodiments, rotate together with the driver shaft 1200. Thus, unlike the embodiment of system 100 (FIGS. 1A and 1B) where the expander 300 is pre-threaded into the sheath in a loading stage (before the sheath 200 is expanded within a bone hole), in the embodiment of system 700 the expander screw 900 need not be pre-coupled to the sheath 800 before the inserter tool 702 is manipulated to insert the expander screw 900 into the sheath 800. An advantage of such a configuration can be that certain design constrains on the expander and the sheath can be eliminated.

The outer shaft 1000 of the tool can have various configurations. For example, the outer shaft 1000 can be similar to outer shaft 400 (FIGS. 1A, 1B, and 4A). Thus, the outer shaft 1000 can have a generally elongate cylindrical shape and can define an inner lumen 1007 extending therethrough between proximal and distal ends 1000*p*, 1000*d* thereof. The inner lumen 1007 can slidably and rotatably receive therein the driver shaft 1200, as shown in FIGS. 7A, 7D, 8A, and 8B.

Similar to outer shaft 400, outer shaft 1000 can have a fork 1001 extending distally from the distal end 1000*d* thereof, as shown in FIGS. 7A, 7B, 7C, and 7D. The fork 1001 of the outer shaft 1000 includes opposed distal first and second prongs 1004, 1006 that can be similar to first and second prongs 404, 406 coupled to outer shaft 400. Thus, the first and second prongs 1004, 1006 can be fixedly coupled to a distal portion 1002*d* of the outer shaft 1000, e.g., by fixedly mating with respective bores extending longitudinally through arms of the distal portion 1002*d*. Alternatively, the first and second prongs 1004, 1006 can be integrally formed with the outer shaft 1000. The prongs 1004, 1006 can be configured to extend along the slots 804*a*, 804*b* in the sheath 800 so as to align a tendon with the sheath 800 and, in embodiments in which the driver shaft 1200 is rotated to insert the expander 900 into the sheath 800, prevent rotation of the sheath 800.

The inner shaft 1100 can also have various configurations. As shown in FIG. 7B, the inner shaft 1100 has a generally elongate cylindrical shape. A distal end 1100*d* of the inner shaft 1100 can be configured to apply a force to a distal end of the sheath 800 (e.g., a distal inner surface of the sheath 800) to advance the sheath 800 and a ligament into the bone hole. A proximal end 1100*p* of the inner shaft 1100 can be fixedly coupled to the outer shaft 1000 via the proximal handle assembly 704, as discussed in more detail below. The inner shaft 1100 can have any suitable size so that it can fit within an inner lumen of the driver shaft 1200 that is, in turn, disposed within the outer shaft 1000. Thus, a diameter of the inner shaft 1100 is less than a diameter of the inner lumen 1203 of the driver shaft 1200.

Figure 7C:
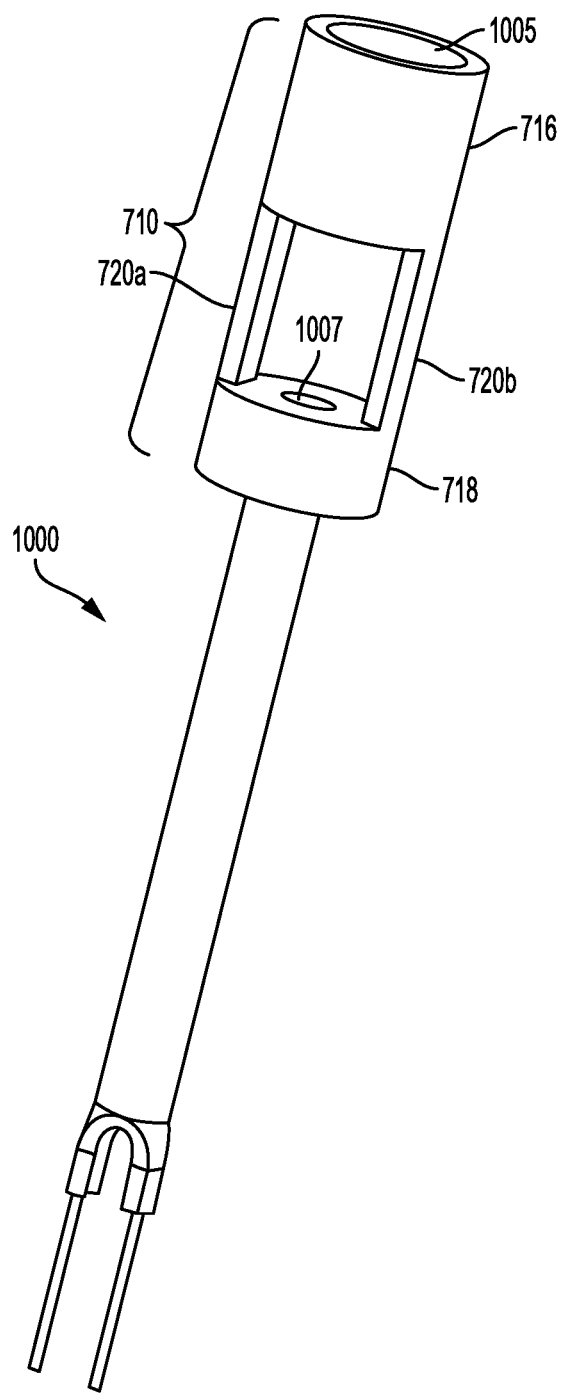
FIG. 7C is a side perspective view of the outer shaft of the inserter tool of the system of FIG. 7A.
Figure 7D:
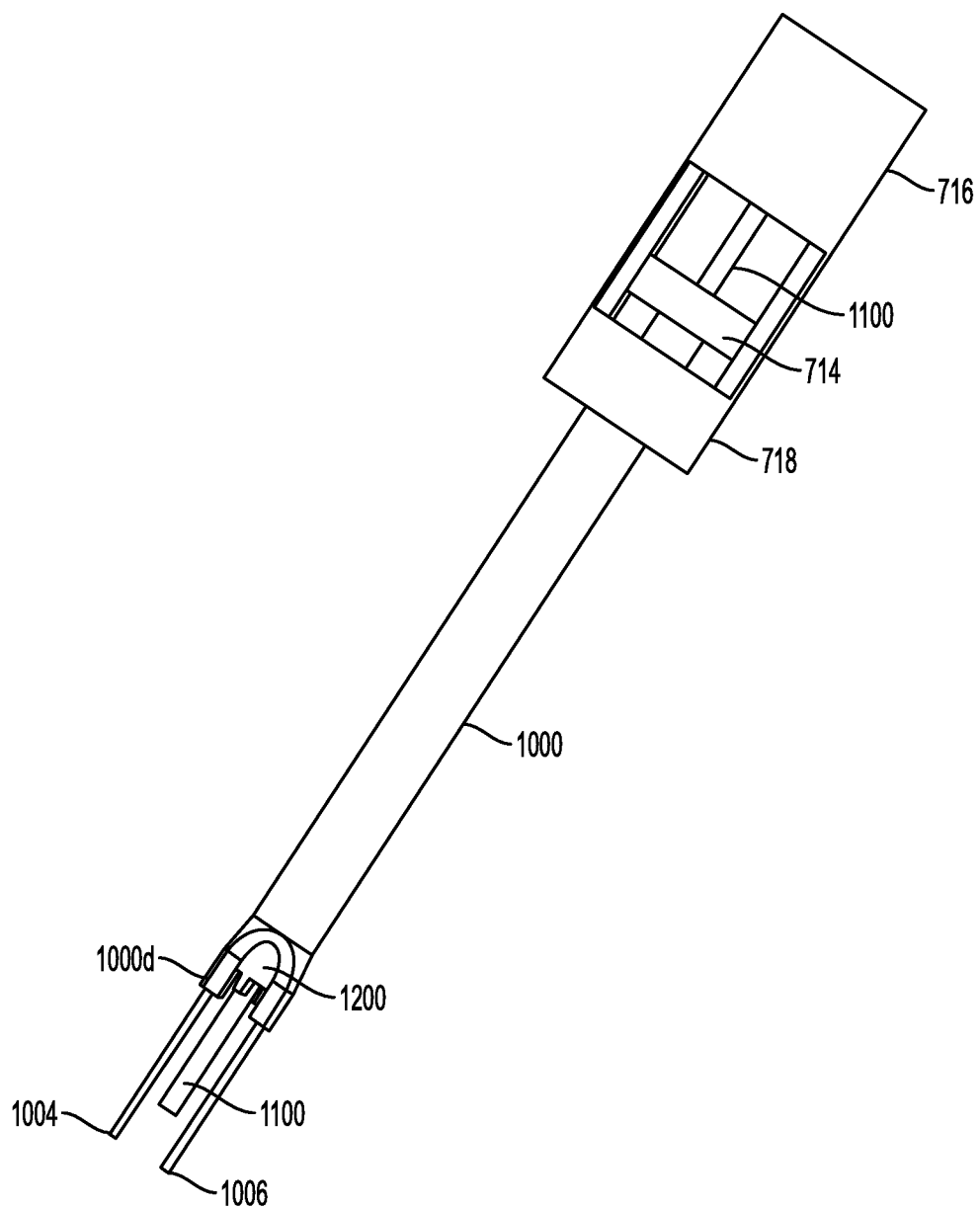
FIG. 7D is a side perspective view of the outer shaft, the driver shaft, and the inner shaft of the inserter tool of the system of FIG. 7A.
Figure 7E:
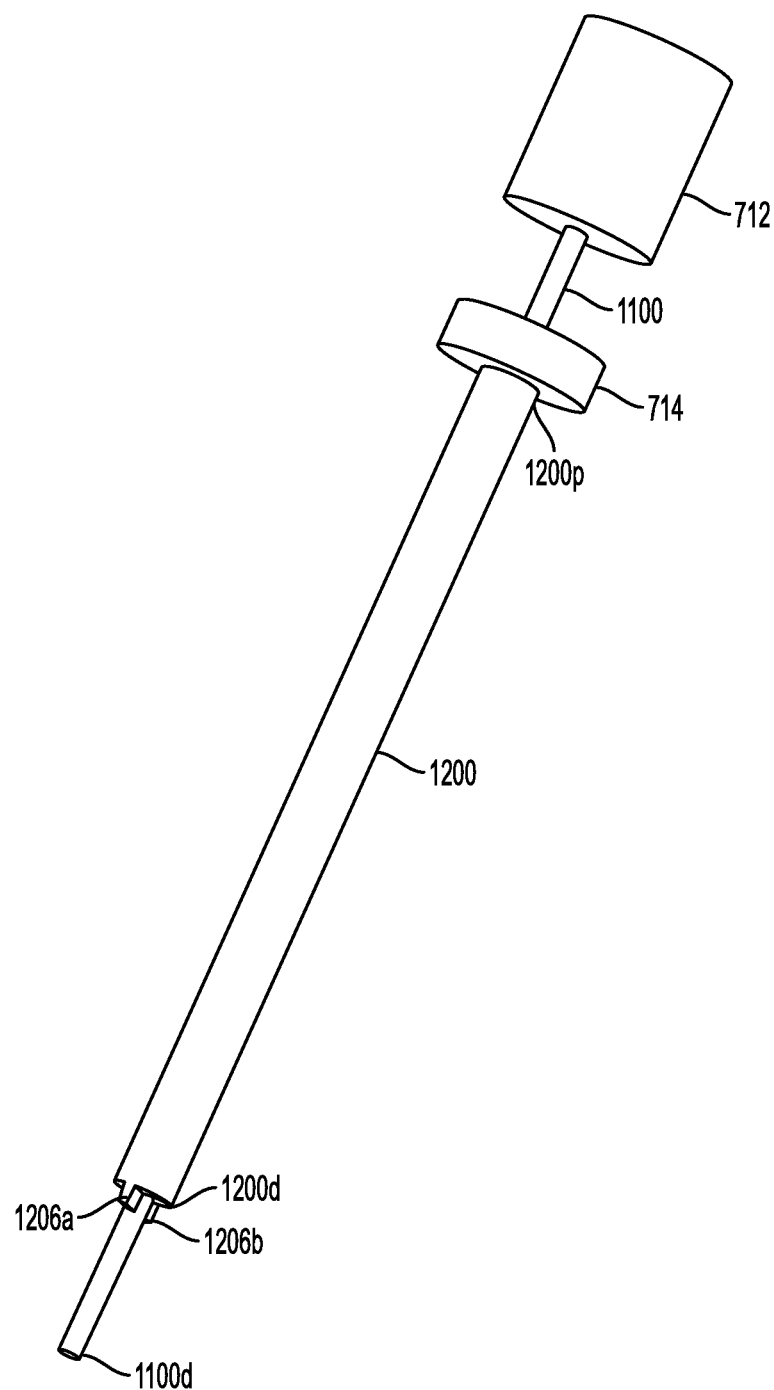
FIG. 7E is a side perspective view of the driver shaft and the inner shaft of the inserter tool of the system of FIG. 7A.

As shown in FIG. 7D, the inner shaft 1100 has a length such that the distal-most end terminates at a location distal to the distal end 1000*d* of the outer shaft 1000 and proximal to a distal-most end of the first and second prongs 1004, 1006. Also, as shown in FIGS. 7D and 7E, the inner shaft 1100 extends through the entire length of the driver shaft 1200 so that the distal end 1100*d* of the inner shaft 1100 extends distally beyond the distal end 1200*d* of the driver shaft 1200 and the proximal end 1100*p* of the inner shaft 1100 extends proximally beyond the proximal end 1200*p* of the driver shaft 1200.

The driver shaft 1200 disposed between the outer shaft 1000 and the inner shaft 1100 can have a variety of configurations. The driver shaft 1200 can be fully cannulated so that it has an inner lumen 1203 extending therethrough. As mentioned above, the lumen 1203 is configured to receive the inner shaft 1100 therein. As shown in FIGS. 7B and 7E, the driver shaft 1200 can have a generally elongate cylindrical shape and it can have an inner lumen with an inner diameter greater than an outer diameter of the inner shaft 1100, and an outer diameter of the driver shaft can be less than an inner diameter of the outer shaft 1000.

In the embodiment illustrated in FIG. 7B, the driver shaft 1200 has the expander 900 coupled to the distal end 1200*d* thereof. The distal end 1200*d* of the driver shaft 1200 can have one or more retaining features configured to removably retain the expander 900 thereon. For example, the distal end 1200*d* can have retaining tabs or protrusions 1206 extending distally therefrom and configured to hold the proximal end of the expander 900 on the driver shaft 1200. In the illustrated embodiment, the driver shaft 1200 has two retaining tabs 1206*a*, 1206*b* (FIG. 7E) configured to retain the expander 900 by a friction fit, snap-fit, or in any other manner. Any suitable number of any retaining features can be used to removably mate the expander 900 so that the expander 900 can be distally translated or both translated and rotated together with the driver shaft 1200. The retaining features can be integrally and/or monolithically formed with driver shaft 1200, or they can be fixedly attached to the driver shaft 1200.

It should be appreciated that the expander 900 can be coupled to the distal end of the driver shaft 1200 without the use of any retaining features. For example, the drive shaft can include a drive tip formed on the distal end thereof and configured to extend into and frictionally engage with a bore in the expander 900. The tip can be configured as a hexagonal or other similar-shaped tip to allow the driver shaft 1200 to rotate the expander 900 into the sheath.

Referring back to FIGS. 7A and 7B, the handle assembly 704 can include a body 710 coupled to the proximal end 1000*p* of the outer shaft 1000, a first handle 712 coupled to the proximal end 1100*p* of the inner shaft 1100, and a second handle 714 coupled to the proximal end 1200*p* of the driver shaft 1200. It should be appreciated that the handles 712, 714 are referred to as "first" and "second" for description purposes only and not to indicate any specific order of assembly or operation of these components. The first and second handles 712, 714 can be coupled to the body 710 in any suitable manner, as embodiments are not limited in this respect. As shown in FIG. 7A, the handle assembly 704 can be configured as a single handle component that can be used to operate the outer, driver, and inner shafts 1000, 1200, 1100.

One skilled in the art will appreciate that the handle assembly 704 can include any other suitable components not shown herein. Furthermore, one skilled in the art will appreciate that the handle assembly 704 is shown by way of example only, as any other handle assembly can be used to operate the inserter tool 702.

As shown in FIG. 7C, the body 710 of the handle assembly 704 is generally cylindrical and includes proximal and distal portions 716, 718 coupled via opposed arms or sidewalls 720*a*, 720*b* extending longitudinally therebetween. The proximal and distal portions 716, 718 can be fully cannulated such that they define lumens 1005, 1007 extending therethrough, respectively. The lumen 1005 in the proximal portion 716 can have a greater diameter than a diameter of the lumen 1007 in the distal portion 718, as shown in FIGS. 7B and 7C.

The arms 720*a*, 720*b* extend rigidly between the portioned and distal portions 716, 718 so as to define a space between the proximal and distal portions 716, 718. The space is preferably sufficient to allow access to the handle 714 and to also allow distal translation of the handle 714 to drive the expander 900 into the sheath 800. The space has a height substantially equal to or greater than a length of the expander such that movement of the handle from a proximal position to a distal position can advance the full length of the expander into the sheath.

As shown in FIGS. 7A-7D, the proximal portion 716 of the body 710 can be in the form of a hollow cylinder. As shown in FIGS. 7A and 7D, the first handle 712 coupled to the proximal end of the inner shaft 1100 can be disposed entirely within the lumen 1005 in the proximal portion 716. The handle 712 can be fixedly coupled within the lumen 1005 in any suitable manner, for example, by threads, press-fitting, snap-fitting, or using any other coupling techniques.

In the illustrated embodiment, the distal portion 718 of the body is shaped as a disk. The inner lumen 1007 extends through the distal portion 718 and is configured to slidably and rotatably receive therein the driver shaft 1200. As shown in FIGS. 7A and 7D, the driver shaft 1200 can be disposed within the lumen 1007 so that the proximal end of the driver shaft 1200 extends proximally beyond a proximal facing surface 719 of the distal portion 718 and the second handle 714 coupled to the driver shaft 1200 is disposed just proximal of the proximal facing surface 719. As shown in FIGS. 7A and 7D, the second handle 714 can be disposed between the arms 720*a*, 720*b* such that it can be rotated and translated within the space defined by the arms 720*a*, 720*b* of the handle assembly 704.

As shown in FIGS. 7A, 7B, 7D, and 7F, the second handle 714 is fixedly coupled to the proximal end of the driver shaft 1200. The illustrated handle 714 is substantial disc-shaped, however, it can various configurations. The handle 714 is fully cannulated such that the inner lumen 1203 extending through the driver shaft 1200 extends through the second handle 714 as well. Such a configuration allows the driver shaft 1200 and the handle 714 to be slidably disposed on the inner shaft 1100, as shown in FIGS. 7A, 7D, and 7E.

The system 700 of FIGS. 7A-7E can be used to implant a sheath or anchor in a bone in various different ways. One exemplary method for implanting an anchor in bone, for example, to perform a biceps tenodesis surgery, is shown in connection with FIGS. 8C, 8D, 9A and 9B. A person of skill in the art will understand that the implant described herein is shown by way of example only, as the illustrated tool can be used with any suitable implant. The method can include retrieving a biceps tendon 1300, determining a size of the tendon, and preparing a bone hole 1302 in bone B similarly to as discussed above in connection with FIG. 6D and/or using any other suitable techniques. Similar to system 100 of FIGS. 1A and 1B, system 700 can be an "all-in-one" device that can used to first "dunk" the tendon 1300 into the bone hole 1302 and to then drive the expander 900 into the sheath 800 to thereby anchor the sheath 800 and the tendon 1300 in the bone hole. It should be appreciated that, although not shown in connection with the described embodiments, in some embodiments, a guidewire can additionally be used.

Figure 8C:
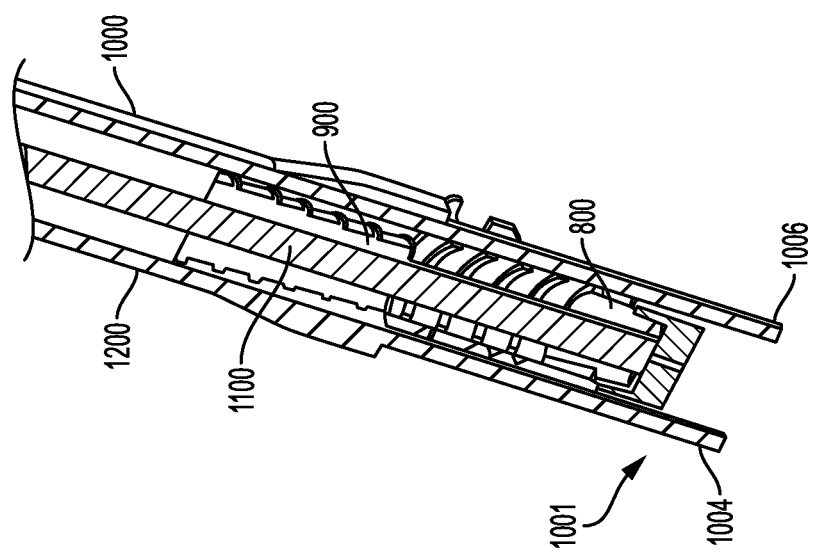
FIG. 8C is a cross-sectional view of a distal portion of the system of FIG. 7A, shown before the expander is advanced into the sheath.
Figure 9B:
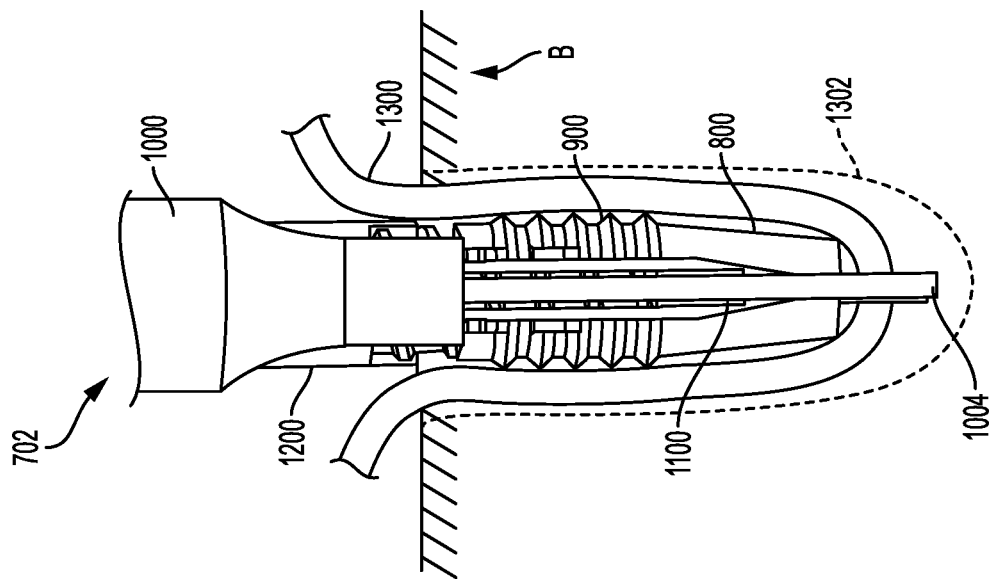
FIG. 9B is a side view of a distal portion of the system of FIG. 7A, shown as being used to insert a tendon into a bone hole in bone.
Figure 9A:
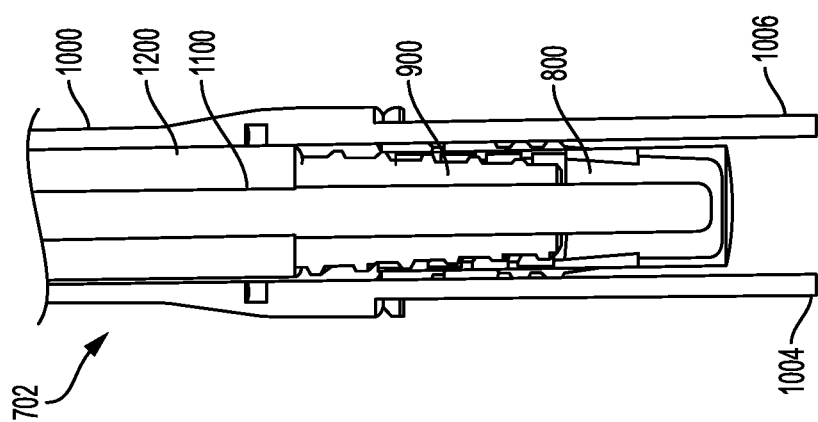
FIG. 9A is a cross-sectional view of a distal portion of the system of FIG. 7A.

In the illustrated embodiment, as shown in FIG. 8C, prior to advancing the expander 900 into the sheath 800, the expander 900 can be coupled to the driver 1200 of the inserter tool 702 such that the expander 900 is proximal of the sheath 800. As a result, the expander and the driver shaft can slide freely relative to the sheath and the outer and inner shafts Like in the system 100 (FIG. 1A), the prongs 1004, 1006 of the distal fork on the outer shaft 1000 extend along the slots in the sheath 800. FIGS. 8D, 9A, and 9B illustrate the inserter tool 702 having the sheath 800 and expander 900 coupled thereto such that the expander 900 and the sheath 800 are disposed over the inner shaft 1100.

Before the sheath is advanced into the bone hole 1302, the inserter tool 702 can be manipulated to position the tendon 1300 between the prongs 1004, 1006 of the fork 1001. The inserter tool 702 can be manipulated to advance, or dunk, the tendon 1300 into the bone hole 1302. Advancement of the inserter tool 702 will cause the distal end of the inner shaft 1100 to abut against a distal inner surface of the sheath 800 and thereby apply force to the distal end of the sheath 800 to advance the sheath 800 and the tendon 1300 into the bone hole 1302. The distal end of the outer shaft can apply a distal force to the sheath, however, the majority of the force is applied to the distal end of the sheath so as to avoid the risk of causing damage to the sheath.

After the inserter tool 702 is used to advance the sheath 800 and the tendon 1300 into the bone hole 1302, the inserter tool 702 can be manipulated to drive the expander 900 into the sheath 800 to expand the sheath 800 and thus anchor it within the bone hole 1302. In the illustrated embodiment, force can be applied to the driver shaft 1200 of the inserter tool 702 to cause the expander 900 removably coupled thereto to advance into the sheath 800. The driver shaft 1200 can translated distally (e.g., by operating handle 714 shown in FIG. 7A) relative to the outer shaft 1000 to cause the expander 900 to be pushed into the sheath 800 to thus expand the sheath 800 outward. In particular, the handle is moved from an initial proximal-most position within the same space in the body to a final distal-most position, in which the handle contacts and abuts against the proximal surface of the distal portion of the body. If the expander includes threads, the driver shaft can additionally be rotated to thread the expander into the sheath. At the same time, the outer shaft 1000 remains stationary as the prongs 1004, 1006 coupled thereto extend into the slots in the sheath 800 prevent the sheath 800 from rotating. Thus, the possibility of twisting the tendon can be eliminated or reduced, which can reduce a risk of damaging the tendon.

When the expander 900 is fully inserted into the sheath 800, the expander 900 will cause the sheath 800 to expand radially outward to engage the tendon 1300 between the sheath 800 and the bone hole 1302, and to thereby anchor the sheath and tendon within the bone hole. The ribs on the outer surface of the sheath can engage bone to prevent back-out. The cortical retaining tabs and/or any other portions of the sheath can also help retain the sheath within the bone hole. Once the sheath 800 is properly anchored into the bone hole to thereby anchor the tendon, the inserter tool 702 can be removed (not shown). Optionally, the engagement between the inner shaft and the expander can be released by pulling the outer shaft 1000 proximally while holding the drive shaft to prevent the sheath and expander from being pulled out of the bone hole.

Figure 10A:
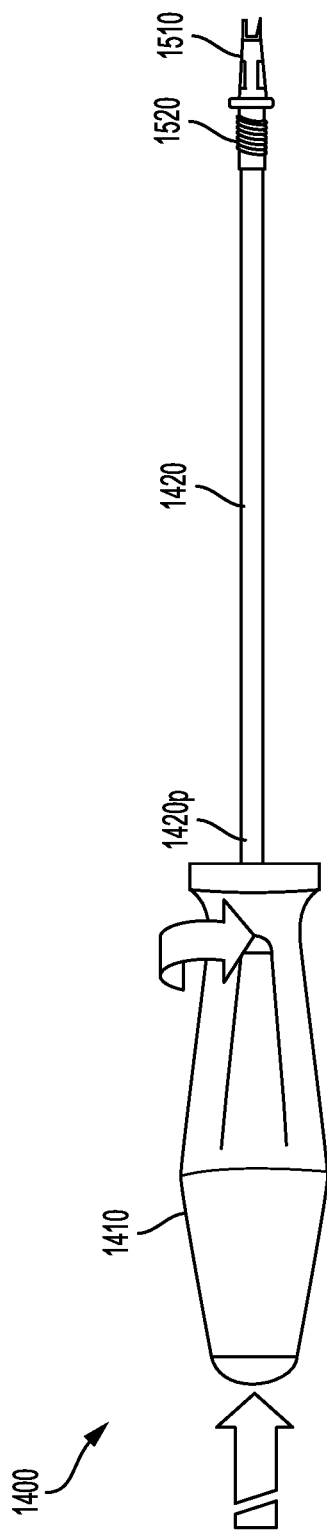
FIG. 10A is a side perspective side view of another embodiment of an inserter tool having a shaft for simultaneously delivering a sheath and an expander into a bone hole.
Figure 10B:
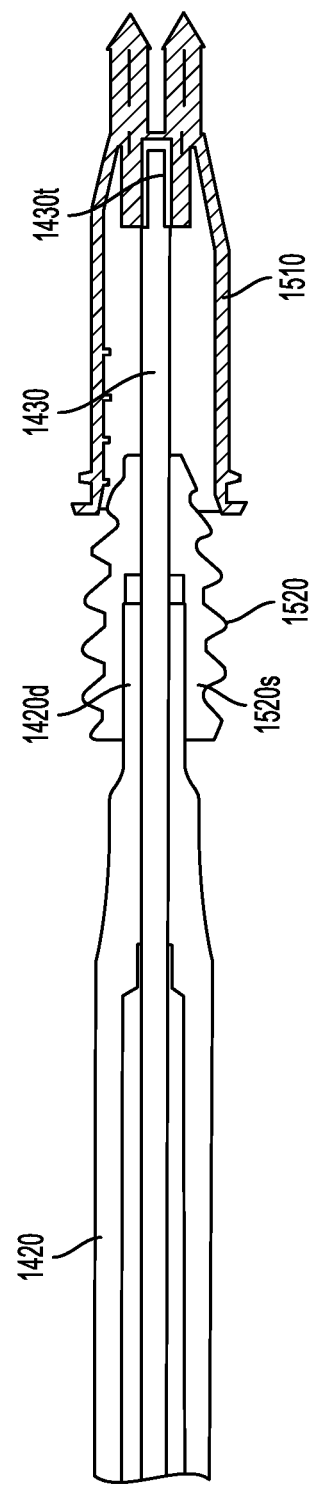
FIG. 10B is a cross-sectional view of a distal portion of the tool, sheath, and expander of FIG. 10A.

FIGS. 10A-10B illustrate another embodiment of an inserter tool 1400 for simultaneously delivering a sheath 1510 and an expander 1520 into a bone hole. In this embodiment, the tool 1400 has a handle 1410 with a single shaft 1420 extending distally from the handle 1410 that is used to both push the sheath 1510 into a bone hole with the expander 1520 trailing behind the sheath 1510, and to rotate and drive the expander 1520 distally into the sheath 1510 to thereby anchor the sheath 1510 within the bone hole. The illustrated implant, which includes the sheath 1510 and the expander 1520, is described in more detail in U.S. patent application Ser. No. 14/610,602 filed on Jan. 30, 2015, and in U.S. patent application Ser. No. 14/610,626 filed on Jan. 30, 2015, which are hereby incorporated by reference in their entireties. A person skilled in the art will appreciate that the implant is shown for illustration purposes only, and that the inserter tool 1400 can be used with various implants.

As shown in FIG. 10A, the handle 1410 of the tool has a generally elongate cylindrical configuration to facilitate grasping. A person skilled in the art will appreciate that the handle 1410 can have any shape suitable for grasping. While not shown, the handle has a lumen extending therethrough and can include features therein for releasably engaging a proximal end of a guidewire, as disclosed in U.S. patent application Ser. No. 14/610,602 filed on Jan. 30, 2015, which is hereby incorporated by reference in its entirety. The handle can also include a bore formed in the distal end thereof for receiving a proximal end of the shaft 1420 to allow the handle 1410 and the shaft 1420 to be fixedly mated to one another.

The shaft 1420 of the tool 1400 can also have a variety of configurations. In the illustrated embodiment, the shaft 1420 has a generally elongate shape with a proximal end 1420$p$ that is mated to the handle 1410. As shown in more detail in FIG. 10B, the shaft 1420 has a distal end in the form of a drive tip 1420$d$ with a reduced diameter such that the drive tip 1420$d$ can extend into and mate with the expander 1520. The shape of the drive tip can vary, but preferably the drive tip 1420$d$ has a shape, such as a hexagonal shape, that allows a rotational force to be applied by the drive tip 1420$d$ to the expander to cause the expander 1520 to rotate. The length of the drive tip 1420$d$ can also vary, but the length is preferably sufficient to allow the drive tip 1420$d$ to extend through a substantial or entire length of a drive socket 1520$s$ formed in the expander 1520.

As further shown in FIG. 10B, the shaft 1420 includes a lumen extending entirely therethrough. The lumen is configured to receive an inner shaft, rod or a guidewire 1430 that extends between the guidewire engaging feature (not shown) in the handle 1410 and the sheath 1510. The guidewire 1430 and the mating connection between both the handle 1410 and the sheath 1510 are described in more detail in the aforementioned applications, but in general the guidewire 1430 has a distal tip 1430$t$ that is configured to releasably mate, e.g., by threads or other mating features, a blind bore formed in a distal end of the sheath 1510. Since the proximal end of the guidewire 1430 is held within the handle 1410, as indicated above, the guidewire 1430 will function to retain the sheath 1510 on the tool 1400.

In use, when the device is fully assembled, the expander 1520 is positioned over the drive tip 1420$d$ on the shaft 1420, which in turn is positioned over the guidewire 1430. The sheath 1510 is mated to the distal end of the guidewire 1430, and the proximal end of the guidewire 1430 is mated within the handle 1410 to thereby retain the sheath 1510 and the expander 1520 on the distal end of the tool 1400. In an exemplary embodiment, as shown, the expander 1520 is at least partially threaded into the sheath 1510 such that rotation of the expander 1520 will cause the expander 1520 to thread distally into the sheath 1510.

The tool 1400 can be used to anchor tissue within a bone hole in accordance with the methods described above and described in the aforementioned applications. In particular, the tool 1400 can be manipulated to advance the sheath 1510 and a tendon positioned between the forks on the distal end of the sheath, into a bone hole. When the handle 1410 is pushed distally, the force will be transferred through the guidewire 1430 to cause the distal end of the guidewire 1430 to push the sheath 1510 into the bone hole. Once the sheath 1510 is fully inserted into the bone hole, e.g., when the tabs at the proximal end of the sheath 1510 abut against the bone surface, the translational coupling between the guidewire 1430 and the tool 1400 can be disengaged and the tool 1400 can be rotated to thereby rotate the expander 1520. The threads on the expander 1520 will thereby drive the expander into the sheath 1510 to expand the sheath outward and thereby anchor the tendon within the bone hole. In an exemplary embodiment, the mating feature inside the handle 1410 allows the tool 1400 to rotate without causing corresponding rotation of the guidewire 1430, and thus without causing rotation of the sheath 1510.

A person skilled in the art will appreciate that the biceps tenodesis methods and devices disclosed herein can be used in a variety of surgical procedures to prevent trauma or damage to a tendon being attached to a bone via a bone hole. The present invention also has application in conventional joint repair surgeries.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method of implanting an anchor in bone, comprising:
    positioning a sheath coupled to a distal end of an outer shaft of an inserter tool adjacent to a ligament to be advanced into a bone hole;
    manipulating the inserter tool to simultaneously advance the sheath and the ligament into the bone hole, the inserter tool having an inner shaft extending through the outer shaft, the inner shaft applying a force to a distal end of the sheath to advance the sheath and the ligament into the bone hole; and
    manipulating the inserter tool to advance an expander disposed over the inner shaft into the sheath, the expander causing the sheath to expand outward and engage the bone hole to thereby anchor the ligament within the bone hole.

2. The method of claim 1, wherein manipulating the inserter tool to advance the expander into the sheath comprises rotating the inner shaft relative to the outer shaft to cause the expander to be threaded into the sheath.

3. The method of claim 2, wherein the inner shaft is prevented from translating relative to the outer shaft.

4. The method of claim 2, wherein the expander is at least partially threaded into the sheath when the sheath is advanced into the bone hole.

5. The method of claim 1, wherein the inner shaft includes a guidewire channel extending therethrough, the guidewire channel configured to allow the sheath, the expander, the inner shaft, and the outer shaft to be slidably advanced over a guidewire.

6. The method of claim 1, wherein the inserter tool includes a handle assembly having a distal handle coupled to a proximal end of the outer shaft, and a proximal handle coupled to a proximal end of the inner shaft.

7. The method of claim 6, wherein the distal handle is configured to prevent axial translation of the inner shaft with respect to the outer shaft.

8. A method of implanting an anchor in bone, comprising:
    positioning a distal end of a sheath coupled to a distal end of an outer shaft of an inserter tool adjacent to a ligament to be advanced into a bone hole, the outer shaft having first and second prongs extending from the distal end of the outer shaft with the ligament positioned therebetween;
    manipulating the inserter tool to advance the sheath and the ligament into the bone hole, the inserter tool having an inner shaft extending through the outer shaft; and
    manipulating the inserter tool to advance an expander disposed over the inner shaft into the sheath, the expander causing the sheath to expand outward and engage the bone hole to thereby anchor the ligament within the bone hole.

9. The method of claim 8, wherein manipulating the inserter tool to advance the expander into the sheath comprises rotating the inner shaft relative to the outer shaft to cause the expander to be threaded into the sheath.

10. The method of claim 9, wherein the inner shaft is prevented from translating relative to the outer shaft.

11. The method of claim 9, wherein the expander is at least partially threaded into the sheath when the sheath is advanced into the bone hole.

12. The method of claim 8, wherein the inner shaft includes a guidewire channel extending therethrough, the guidewire channel configured to allow the sheath, the expander, the inner shaft, and the outer shaft to be slidably advanced over a guidewire.

13. The method of claim 8, wherein the inserter tool includes a handle assembly having a distal handle coupled to a proximal end of the outer shaft, and a proximal handle coupled to a proximal end of the inner shaft.

14. The method of claim 13, wherein the distal handle is configured to prevent axial translation of the inner shaft with respect to the outer shaft.

* * * * *